United States Patent
Urano et al.

(10) Patent No.: US 8,804,110 B2
(45) Date of Patent: Aug. 12, 2014

(54) FAULT INSPECTION DEVICE AND FAULT INSPECTION METHOD

(75) Inventors: Yuta Urano, Yokohama (JP); Shigenobu Maruyama, Oiso (JP); Toshiyuki Nakao, Yokohama (JP); Toshifumi Honda, Yokohama (JP); Yukihiro Shibata, Fujisawa (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/703,414

(22) PCT Filed: May 20, 2011

(86) PCT No.: PCT/JP2011/002810
§ 371 (c)(1),
(2), (4) Date: Jan. 30, 2013

(87) PCT Pub. No.: WO2012/014358
PCT Pub. Date: Feb. 2, 2012

(65) Prior Publication Data
US 2013/0141715 A1 Jun. 6, 2013

(30) Foreign Application Priority Data
Jul. 30, 2010 (JP) .................................. 2010-171333

(51) Int. Cl.
*G01N 21/00* (2006.01)
*G01N 21/95* (2006.01)
*G01N 21/94* (2006.01)
*G01N 21/956* (2006.01)

(52) U.S. Cl.
CPC ............ *G01N 21/9501* (2013.01); *G01N 21/94* (2013.01); *G01N 21/956* (2013.01)
USPC .................. 356/237.2; 356/237.3; 356/237.4; 356/237.5

(58) Field of Classification Search
CPC .. G01N 21/9501; G01N 21/94; G01N 21/956
USPC ............................................ 356/237.1–237.5
See application file for complete search history.

(56) References Cited

U.S. PATENT DOCUMENTS

| | | | |
|---|---|---|---|
| 5,903,342 | A | 5/1999 | Yatsugake et al. |
| 6,608,676 | B1 | 8/2003 | Zhao et al. |

(Continued)

FOREIGN PATENT DOCUMENTS

| | | |
|---|---|---|
| JP | 7-229845 | 8/1995 |
| JP | 9-304289 | 11/1997 |

(Continued)

*Primary Examiner* — Michael P Stafira
(74) *Attorney, Agent, or Firm* — Antonelli, Terry, Stout & Kraus, LLP.

(57) ABSTRACT

Proposed is a defect inspection method whereby: illuminating light having a substantially uniform illumination intensity distribution in one direction of a sample surface irradiated on the sample surface; multiple scattered light components, which are output in multiple independent directions, are detected among the scattered light from the sample surface and multiple corresponding scattered light detection signals are obtained; at least one of the multiple scattered light detection signals is processed and the presence of defects is determined; at least one of the multiple scattered light detection signals that correspond to each of the points determined by the processing as a defect is processed and the dimensions of the defect are determined; and the position and dimensions of the defect on the sample surface, at each of the points determined as a defect, are displayed.

8 Claims, 15 Drawing Sheets

(56) References Cited

U.S. PATENT DOCUMENTS

| | | |
|---|---|---|
| 7,385,688 B1 | 6/2008 | Kadkly et al. |
| 7,869,024 B2 * | 1/2011 | Urano et al. ............... 356/237.2 |
| 2005/0185172 A1 | 8/2005 | Ishimaru et al. |
| 2006/0256325 A1 | 11/2006 | Mcmillan et al. |
| 2009/0257058 A1 | 10/2009 | Urano et al. |

FOREIGN PATENT DOCUMENTS

| | | |
|---|---|---|
| JP | 2005-156516 | 6/2005 |
| JP | 2006-201179 | 8/2006 |
| JP | 2009-244035 | 10/2009 |
| WO | WO 2008/108174 A1 | 9/2008 |

* cited by examiner

SCHEMATIC DIAGRAM OF ILLUMINATION INTENSITY DISTRIBUTION ON SAMPLE SURFACE

FAULT INSPECTION DEVICE AND FAULT INSPECTION METHOD

TECHNICAL FIELD

The present invention relates to a defect inspection device and a defect inspection method with which a minute defect present on a sample surface is inspected and a type and dimensions of the defect are determined and output.

BACKGROUND ART

In order to maintain and/or increase a product yield in a line for manufacturing a semiconductor substrate, a thin-film substrate, or the like, inspection is performed for a defect present on the surface of the semiconductor substrate, the thin-film substrate, or the like. As prior-art defect inspection techniques, Patent Literature 1 (JP-A-9-304289), Patent Literature 2 (JP-A-2006-201179), Patent Literature 3 (U.S. Patent Publication No. 2006/0256325), and so on are known. These are the techniques in which illumination light is focused into dimensions of several tens of μm on the sample surface to detect a minute defect, light scattered by the defect is collected and detected, and the defect of dimensions equal to or more than a range of several tens of nm to several μm is inspected. By moving a stage which holds a sample (an inspection target) thereon rotationally and translationally, an illumination spot is spirally scanned on the surface of the sample, whereby the full surface of the sample is inspected.

In the Patent Literature 1 and 2, there are described techniques for detecting components of light scattered by a defect emitted at a high angle and emitted at a low angle, and classifying a type of the defect depending on their ratio.

Further in the Patent Literature 2, there is described a technique for calculating dimensions of the detected defect based on an intensity of light scattered by the defect.

Also, in the Patent Literature 3, there is described, in order to reduce thermal damage applied to a sample, controlling a power of illumination light, a scan speed of an illumination spot, or dimensions of the illumination spot while inspecting an inspection target. More specifically, it is described that the thermal damage applied to the sample is assumed to be determined by a product of an illumination power density and an irradiation time and, in order not to make it exceed a certain value, the power of the illumination light, the scan speed of the illumination spot, or the dimensions of the illumination spot are varied according to a radial position on the sample while scanning.

As a technique for inspecting a sample in a short time by illuminating a large area of the sample surface with a Gaussian beam elongated in one direction and detecting an illumination area at once using a detector with a plurality of pixels such as a CCD, Patent Literature 4 (U.S. Pat. No. 6,608,676) is known.

As a technique for shaping illumination light into a shape that a plurality of illumination spots are arranged on the surface of an inspection target using an aspherical lens or a diffractive optical element in oblique incidence illumination, Patent Literature 5 (U.S. Pat. No. 7,385,688) is known.

CITATION LIST

Patent Literature

Patent Literature 1: JP-A-9-304289
Patent Literature 2: JP-A-2006-201179
Patent Literature 3: U.S. Patent Publication No. 2006/0256325
Patent Literature 4: U.S. Pat. No. 6,608,676
Patent Literature 5: U.S. Pat. No. 7,385,688

SUMMARY OF INVENTION

Technical Problem

The defect inspection used in processes of manufacturing a semiconductor or the like requires detection of a minute defect, measurement of dimensions of the detected defect with a high accuracy, inspection of a sample in a non-destructive manner (or without causing degeneration of the sample), acquisition of constant inspection results (the number of detected defects, positions, dimensions, defect types) when the same sample is inspected, inspection of many samples in a certain time, and so on.

In the techniques described in the aforementioned Patent Literature 1, 2, 4, and 5, particularly with respect to minute defects having dimensions of 20 nm or less, light scattered by such defects becomes extremely faint, and thus it is impossible to detect since a defect signal is buried in noise caused by scattered light generated on the surface of the sample, noise of a detector, or noise of a detection circuit. Otherwise, when the illumination power is increased to avoid the above problem, increase in the temperature of the sample by the illumination light becomes great and thermal damage to the sample arises. Instead, when the scan speed of the samples is lowered to avoid the above, a surface area of samples or the number of samples capable of being inspected is decreased. For the above, it was difficult to detect minute defects at a high speed while avoiding the thermal damage.

Further, when spiral scanning is performed with a constant rotational speed of a sample, the moving speed of an illumination spot becomes minimal at the center of the sample, which results in that thermal damage at the center of the sample becomes great. To avoid this, there is such a means as to scan while a linear speed at the scanning position is kept constant, as to perform XY scanning, or the like so that the irradiation time would not vary with the position of the sample. In the former means, inspection of the central part becomes substantially impossible because an infinitely large rotational speed is required for the inspection of the central part of the sample. In the latter means, since a time is required in acceleration and/or deceleration of a stage upon changeover of directions of main scanning and sub scanning, there is a problem that the full surface inspection of the sample requires a long time.

Also, since an illumination light intensity distribution in the illumination spot is set as a Gaussian distribution, there is another problem that the signal intensity of scattered light of a detected defect varies according to a relative position of the defect with respect to the illumination spot, whereby a defect detection sensitivity fluctuates and a defect dimension calculation accuracy is reduced.

Furthermore, when the illumination light intensity distribution in the illumination spot is set as a Gaussian distribution, there is a problem that inspection of the area close to an edge of a semiconductor substrate or the like with a high sensitivity becomes difficult as a side lobe of a Gaussian distribution comes to the edge of the semiconductor substrate or the like and scattered light of a large intensity is generated to become noise upon inspection of the area close to the edge of the semiconductor substrate or the like as an inspection target.

Meanwhile, the technique disclosed in the Patent Literature 3 is intended to reduce thermal damage in the vicinity of the center of the sample as compared with the prior art or to increase a defect detection sensitivity at the outer periphery of the sample while suppressing thermal damage in the vicinity of the center of the sample to a level similar to the prior art by changing the illumination power in proportion to a radial position on the sample. However, since the thermal damage is assumed to be proportional to a product of the illumination power density and the irradiation time, there is a problem which is explained in the following.

First, since no consideration is paid to an influence of thermal diffusion from the illumination spot in estimation of thermal damage, thermal damage at the center of a sample having a particularly long irradiation time is overestimated than the reality. Thus, the illumination power is decreased more than needed at the center of the sample and a defect detection sensitivity is decreased.

Second, in order to prevent thermal damage from taking place on the entire surface of a sample, it is necessary to prescribe an illumination power to be provided with a criterion that no damage takes place at the center of the sample where thermal damage becomes maximal. However, since a scan speed (a linear speed) is zero at the center of the sample in the rotational scan, the irradiation time in calculation diverges to infinity, thus resulting in that it is impossible to quantitatively estimate thermal damage on the aforementioned assumption and the illumination power can not be prescribed. Inversely, in order to ensure that no thermal damage at the center takes place, the illumination power needs to be set to zero, thus disabling inspection of the center.

Further, when the illumination power is varied with a radial position on a sample as in Patent Literature 3, since a peak value in a scattered light signal varies depending on a position on the sample even for defects having the same dimensions, there occur problems such as a varying defect detection sensitivity and a reduced defect dimension calculation accuracy because a signal is saturated for a defect located on the outer periphery of the sample, a peak value for a defect located at the center is too small to be detected, or the like.

Moreover, when the shape of an illumination spot is dynamically varied with a radial position on the sample during inspection as in Patent Literature 3, since the obtained shape of the illumination spot depends upon differences among individuals of optical elements in an illumination optics upstream, upon an accuracy of control, or the like, it becomes difficult to accurately control the shape of the illumination spot or to perform similar control of the shape of the illumination spot among a plurality of devices.

In addition, as in Patent Literature 4, a method of obtaining an illumination intensity distribution formed in a line elongated in one direction on the surface of an inspection target using a group of lenses placed in parallel to the surface of the inspection target in oblique-incidence illumination has a problem that, when the incidence angle of the illumination is larger than 65 degrees, it is difficult to form a desired illumination intensity distribution, in particular, a thin line-shaped illumination spot having a width of 5 µm or less in a shorter-axis direction due to difficulty in suppression of off-axis aberration, so that a high inspection sensitivity can not be obtained.

As in Patent Literature 5, furthermore, when a technique of scanning with a plurality of illumination spots arranged in row is applied to a spiral scanning suitable for high-speed inspection, overlap and/or reversal of scan loci among illumination spots occur depending on a radial position on a sample due to differences in curvatures of the scan loci. There is a problem that an inspection efficiency (an area to be inspected per unit time) is reduced as result.

Besides, as in Patent Literature 5, when the shape of an illumination spot is shaped using an aspherical lens or a diffractive optical element, a slight positional deviation, an angular deviation, an intensity distribution disturbance, or a wavefront disturbance in light entering the aspherical lens or the diffractive optical element causes the shape of the illumination spot output therefrom to vary, thus making acquisition of a stable inspection result difficult.

Solution to Problem

Outlines of the invention disclosed in the present application in order to solve the aforementioned problems are exemplified as follows.

(1) A defect inspection device includes an irradiating unit, the irradiating unit including: an illumination light adjusting unit which adjusts light emitted from a light source into illumination light having predetermined irradiation conditions; and an illumination intensity distribution control unit which controls an illumination intensity so that an illumination intensity in a predetermined detection target area out of an illumination area on a surface of a sample on which the illumination light is irradiated is 50% or more of an illumination intensity at a center position of the illumination light on a surface of the sample and an illumination intensity in an illumination area other than the predetermined detection target area is 0.1% or less of an illumination intensity at a center position of the illumination light on a surface of the sample; a scanning unit which scans the sample in a direction perpendicular to a longitudinal direction of the illumination area in the irradiating unit; a detecting unit which detects scattered light generated from a surface of the sample due to illumination light irradiated by the irradiation unit; and a determining unit, the determining unit including a defect presence/absence determining unit which processes a detection signal based on scattered light from a surface of the sample detected by the detecting unit and determines presence/absence of a defect on a surface of the sample; and a defect dimension determining unit which determines, when presence of a defect is determined by the defect presence/absence determining unit, a dimension of the defect.

Advantageous Effects of Invention

In accordance with the present invention, it is possible to scan an entire surface of a sample in a short time, detect a minute defect while reducing thermal damage to the sample, calculate dimensions of the detected defect with a high accuracy, and output a stable inspection result.

DESCRIPTION OF EMBODIMENTS

Figure 1:
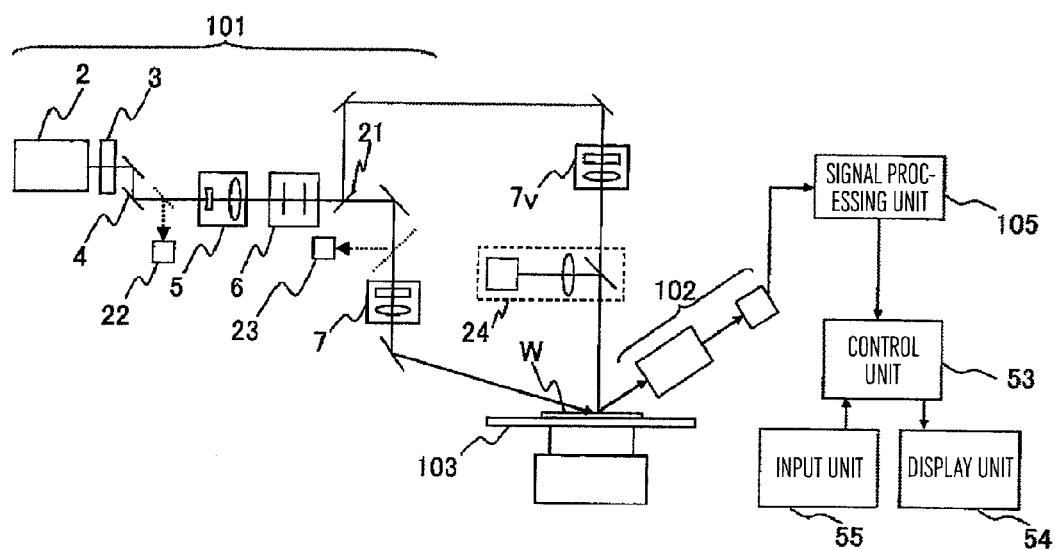
FIG. 1 is a configuration diagram of an entire scheme showing an embodiment of a defect inspection device according to the present invention.

An example of a schematic configuration of an embodiment of the present invention is explained with reference to FIG. 1. It comprises appropriately an illumination unit 101, a detection unit 102, a stage 103 capable of mounting a sample W thereon, a signal processing unit 105, a control unit 53, a display unit 54, and an input unit 55. The illumination unit 101 properly comprises a laser light source 2, an attenuator 3, an exit light adjustment part 4, a beam expander 5, a polarization control part 6, and an illumination intensity distribution control part 7. A laser light beam emitted from the laser light source 2 is adjusted with the attenuator 3 into a desired beam intensity, adjusted by the exit light adjustment part 4 into a desired beam position and a desired beam travelling direction, adjusted by the beam expander 5 into a desired beam diameter, adjusted by the polarization control part 6 into a desired polarization state, adjusted by the illumination intensity distribution control part 7 into a desired intensity distribution, and then irradiated on an inspection target area of the sample W.

By a position and an angle of a reflecting mirror of the exit light adjustment part 4 arranged in an optical path in the illumination unit 101, the incidence angle of illumination light with respect to the surface of the sample is determined. The incidence angle of the illumination light is set at an angle suitable for detection of a minute defect. The larger the illumination incidence angle is, that is, the smaller the illumination elevation angle (made between the surface of the sample and an axis of the illumination light) is, the weaker scattered light (called haze) from fine irregularities on the surface of the sample, which becomes noise for scattered light from minute foreign objects on the sample surface, is and the more preferable for detection of a minute defect it is. For this reason, when the scattered light from the minute irregularities on the sample surface prevents the detection of a minute defect, it is preferable to set the incidence angle of illumination light at an angle of 75 degrees or more (that is, an elevation angle of 15 degrees or less). On the other hand, the smaller the illumination incidence angle is in oblique incidence illumination, the greater an absolute amount of the scattered light from minute foreign objects is; therefore, when shortage of an amount of scattered light from the defect prevents detection of the minute defect, it is preferable to set the incidence angle of the illumination light at an angle of 60 degrees or more and 75 degrees or less (that is, the elevation angle of 15 degrees or more and 30 degrees or less). Further when oblique incidence illumination is executed, by setting the polarization of illumination as P polarization by polarization control of the polarization control part 6 in the illumination unit 101, the scattered light from the defect on the sample surface can be increased compared with other polarizations.

Also, as the need arises, by inserting a mirror 21 in the optical path of the illumination unit 101 and arranging other mirrors properly as shown in FIG. 1, the optical path of illumination is changed so that the illumination light is irradiated from a direction substantially normal to the sample surface (normal illumination). In this case, an illumination intensity distribution on the sample surface is controlled by an illumination intensity distribution control part 7v similar to the oblique incidence illumination. In order to obtain oblique incidence illumination and scattered light from a defect of a form of depression (such as polishing scar or a crystal defect in a crystalline material) on the face of the sample by inserting a beam splitter at the same position as the mirror 21, the normal illumination which enters substantially normal to the sample surface is suitable. Incidentally, an illumination intensity distribution monitor 24 shown in FIG. 1 is explained later in detail.

As the laser light source 2, one which oscillates laser beam of ultraviolet or vacuum ultraviolet of a short wavelength (having a wavelength equal to or shorter than 355 nm) as a wavelength hard to penetrate into an interior of a sample, and provides a high output equal to or greater than 2 W, is used in order to detect a minute defect in the vicinity of the surface of the sample. The diameter of an exit beam is about 1 mm. In order to detect a defect in the interior of the sample, one which oscillates laser beam of visible or infrared as a wavelength easy to penetrate into the interior of the sample is used.

The attenuator 3 properly comprises a first polarizing plate, a half-wave plate rotatable around the optical axis of the illumination light, and a second polarizing plate. Light entering into the attenuator 3 is converted by the first polarizing plate into linearly polarized light, is rotated to an arbitrary direction of a polarization direction according to the azimuth angle of the slow axis of the half-wave plate, and then passes through the second polarizing plate. A light intensity is reduced at an arbitrary ratio by controlling the azimuth angle of the half-wave plate. When light entering into the attenuator 3 has a sufficiently high degree of linear polarization, the first polarizing plate is not necessarily required. As the attenuator 3, one for which a relationship between an input signal and an attenuation rate is corrected in advance is employed. As the attenuator 3, it is also possible to use an ND filter having a gradation density distribution.

The exit light adjustment part 4 comprises a plurality of reflecting mirrors. Although explanation is given herein for an embodiment which is constructed with two reflecting mirrors, it is not limited thereto; three or more reflecting mirrors may properly be employed. Here, a three-dimensional Cartesian coordinate system (XYZ coordinates) is provisionally defined and it is assumed that incident light into the reflecting mirror is travelling to the +X direction. The first reflecting mirror is installed so as to deflect the incident light to the +Y direction (incidence and reflection in the XY plane), and the second reflecting mirror is installed so as to deflect light reflected by the first reflecting mirror to the +Z direction (incidence and reflection in the YZ plane). By translational movements and angle adjustments of respective reflecting mirrors, the position and the travelling direction (angle) of light emitted from the exit light adjustment part 4 are adjusted. By taking an arrangement in which the plane of incidence/reflection (the XY plane) of the first reflecting mirror and the plane of incident/reflection (the YZ plane) of the second reflecting mirror are perpendicular to each other as mentioned above, adjustment of the position and the angle in the XZ plane and adjustment of the position and the angle in the YZ plane of the light exiting from the exit light adjustment part 4 can be performed independently.

The beam expander 5 comprises two or more groups of lenses and has a function of expanding the diameter of an incident collimated light flux. For example, a Galilean type beam expander comprising a combination of a concave lens and a convex lens is used. The beam expander 5 is installed to a translating stage having two or more axes and the position can be adjusted to make a predetermined beam position and the center coincide with each other. The beam expander 5 is provided with a function of angle adjustment as whole to make the optical axis of the beam expander 5 and the optical axis of a predetermined beam coincide with each other. By adjusting an interval between lenses, a magnification ratio of the diameter of the light flux can be controlled (a zoom mechanism). When light incident into the beam expander 5 is not collimated, the magnification of the diameter of the light flux and collimation (quasi-collimation of the light flux) are simultaneously carried out by adjustment of an interval between lenses. The collimation of the light flux may be carried out by installing a collimate lens upstream of the beam expander 5 independently of the beam expander 5. A magnification ratio of the beam diameter by the beam expander 5 is from about 5 to about 10, and a beam emitted from the light source and having a diameter of 1 mm is enlarged from about 5 mm to about 10 mm.

The polarization control part 6 is configured with a half-wave plate and a quarter-wave plate, and controls the polarization state of illumination light into an arbitrary polarization state. The states of light incident into the beam expander 5 and light incident into the illumination intensity distribution control part 7 are measured with beam monitors 22 and 23 in the midway of the optical path in the illumination unit 101.

Figure 2:
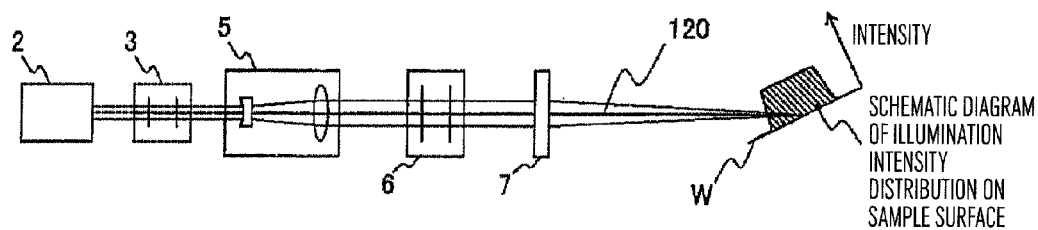
FIG. 2 is a diagram showing an example of a shape of an illumination intensity distribution implemented with an illumination unit of the defect inspection device according to the present invention.
Figure 3:
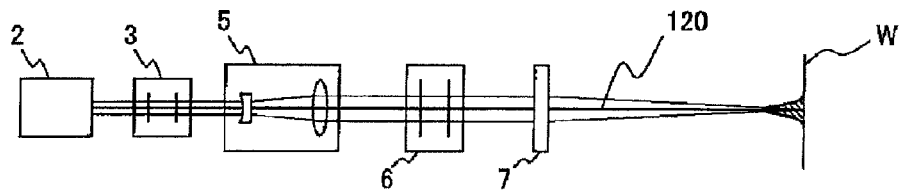
FIG. 3 is a diagram showing a modified example of the shape of the illumination intensity distribution implemented with the illumination unit of the defect inspection device according to the present invention.

In FIGS. 2 to 6, schematic diagrams of positional relationships between an axis 120 of illumination light guided onto the surface of a sample from the illumination unit 101 and a shape of an illumination intensity distribution. Incidentally, the configuration of the illumination unit 101 in FIGS. 2 to 6 is shown only partly, and the exit light adjustment part 4, the mirror 21, the beam monitors 22 and 23, and the like are omitted. In FIG. 2 a schematic diagram of a cross section of an incident plane (a plane including an axis of illumination light and a normal of a sample surface) of oblique incidence illumination is shown. The oblique incidence illumination is tilted with respect to the sample surface in an incident plane. A substantially uniform illumination intensity distribution is generated by the illumination unit 101 in the incident plane. A length of a part where the illumination intensity is uniform is from about 100 μm to about 1 mm in order to inspect a wide area per unit time. In FIG. 3 a schematic diagram of a cross section of a plane including the normal of the sample surface and perpendicular to the incident plane of the oblique incidence illumination is shown. In this plane, an illumination intensity distribution on the face of the sample forms an illumination intensity distribution in which an intensity at the periphery is weak relative to the center thereof. More specifically, it becomes a Gaussian distribution reflecting the intensity distribution of light incident on the illumination intensity distribution control part 7, or a distribution similar to a first-order Bessel function of the first kind or a sinc function reflecting the shape of the aperture of the illumination intensity distribution control part 7. In order to reduce haze generated from the sample surface, the length of the illumination intensity distribution in this plane (the length of an area having an illumination intensity equal to or greater than 13.5% of the maximum illumination intensity) is shorter than the length of a part where the illumination intensity in the incident plane is uniform and is from about 5 μm to about 20 μm. The illumination intensity distribution control part 7 comprises optical elements such as an aspheric lens, a diffractive optical element, a cylindrical lens array, and a light pipe, which are described later. Optical elements constituting the illumination intensity distribution control part 7 are installed perpendicular to the axis of the illumination light as shown in FIGS. 2 and 3.

Figure 7:
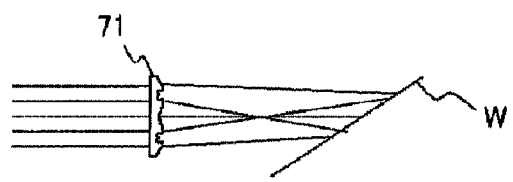
FIG. 7 is a diagram showing an example of an optical element comprised in an illumination intensity distribution control part of the defect inspection device according to the present invention.

The illumination intensity distribution control part 7 comprises optical elements which act on the phase distribution and the intensity distribution of incident light. As an optical element constituting the illumination intensity distribution control part 7, a diffractive optical element 71 (DOE: Diffractive Optical Element) is used (FIG. 7). The diffractive optical element 71 is one in which a fine undulating shape having a dimension similar to or smaller than the wavelength of the light is formed on a substrate made of a material allowing incident light to transmit therethrough. As the material allowing incident light to transmit, fused quartz is used for ultraviolet light. In order to suppress attenuation of light passing through the diffractive optical element 71, one with an anti-reflective film coated thereon is preferably employed. For formation of the aforementioned fine undulating shape, a lithography method is used. By making the light which becomes quasi-collimated after passing through the beam expander 5 passing through the diffractive optical element 71, an on-sample-plane illumination intensity distribution according to the undulating shape of the diffractive optical element 71 is formed. The undulating shape of the diffractive optical element 71 is designed and manufactured to a shape obtained based on calculation using the Fourier optics theory so that the illumination intensity distribution formed on the sample surface becomes a long uniform distribution on the aforementioned incident plane. The optical elements comprised in the illumination intensity distribution control part 7 are equipped with a mechanism of adjusting translations of two or more axes and a mechanism of adjusting rotations of two or more axes so that a relative position and angles with respect to the optical axis of the incident light can be adjusted. Further, a focus adjusting mechanism based on movement in the optical axis direction is provided.

Figure 14:
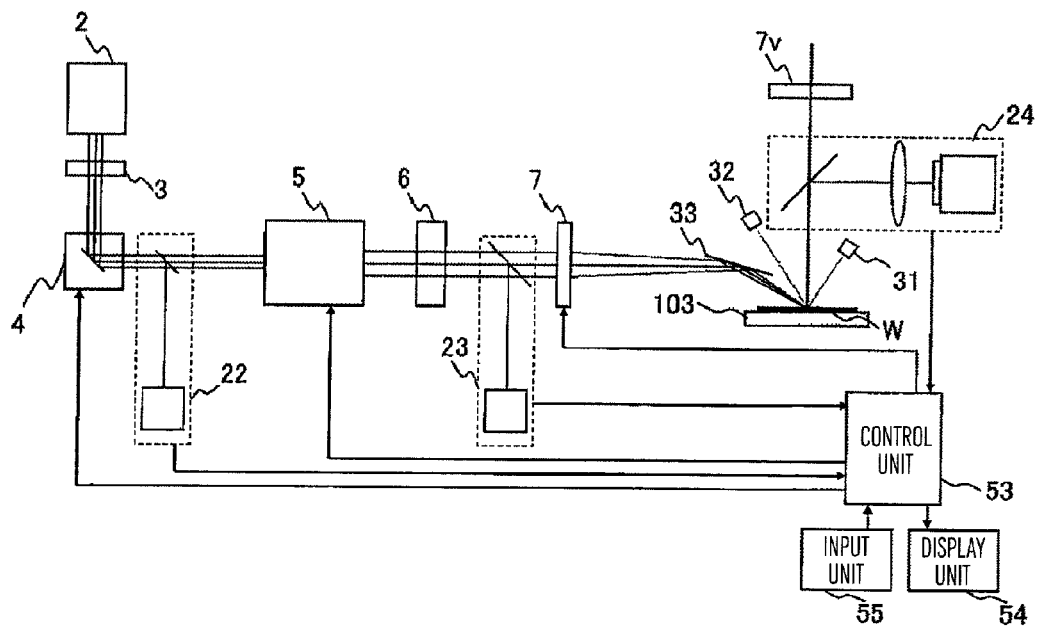
FIG. 14 is a diagram showing an example of a means for measuring and adjusting a status of illumination light in the illumination unit of the defect inspection device according to the present invention.

An illumination light state measuring means in the illumination unit 101 is explained with reference to FIG. 14. The beam monitor 22 measures and outputs a position and angles (a travelling direction) of illumination light passing through the exit light adjustment part 4. The beam monitor 23 measures and outputs a position and a wavefront of illumination light entering the illumination intensity distribution control part 7.

The position measurement of the illumination light at the beam monitor 22 is carried out by measuring the centroid position of a light intensity of the illumination light. As a specific position measurement means, a PSD (Position Sensitive Detector) or an image sensor such as a CCD sensor or a CMOS sensor is used. The angle measurement of the illumination light at the beam monitor 22 is carried out with a position sensitive detector or an image sensor installed at a position further away from the light source than the position measurement means described above. The illumination light position and the illumination light angle measured at the beam monitor 22 are input to the control unit 53 and displayed on the display unit 54. When the position or the angle of the illumination light is off from a predetermined position or angles, respectively, it is adjusted in the exit light adjustment part 4 so as to return to the predetermined position.

Figure 15:
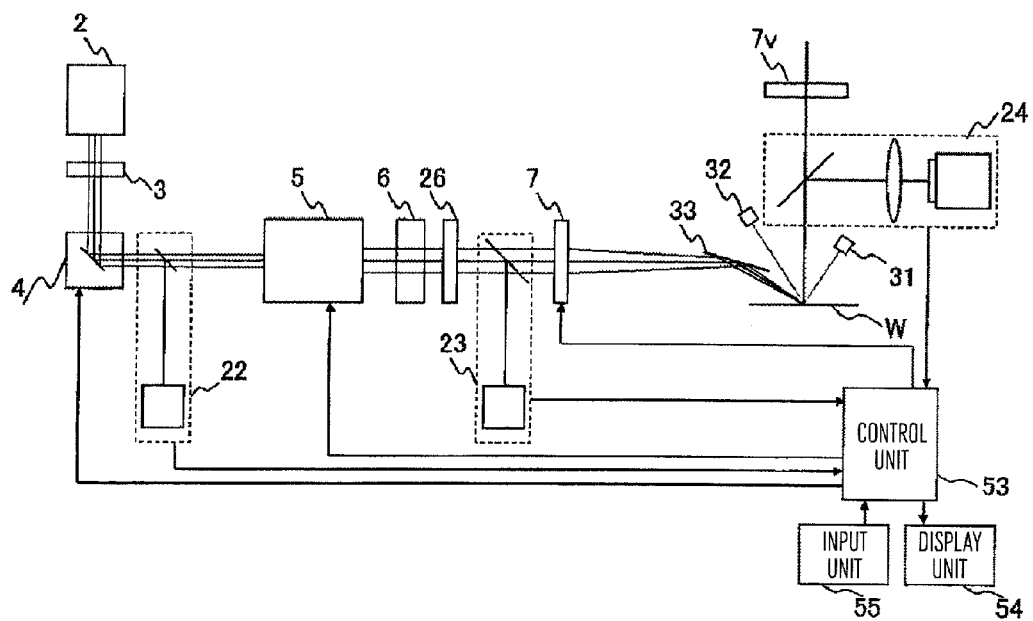
FIG. 15 is a diagram showing a modified example of the means for measuring and adjusting the status of illumination light in the illumination unit of the defect inspection device according to the present invention.

The position measurement of the illumination light at the beam monitor 23 is carried out by a means similar to the position measurement means at the beam monitor 22. Since the beam diameter is expanded to equal to or more than several mm at the measurement target position of the beam monitor 23, however, the position measurement is carried out with the measurement target position reduced and projected on a light receiving surface of a detector of a position measurement means such as a position sensitive detector as necessary. The wavefront measurement of the illumination light at the beam monitor 23 is carried out to measure a parallelism of light incident on the illumination intensity distribution control part 7. Measurement with a shearing interferometer or measurement with a Shack-Hartmann wavefront sensor is carried out for the illumination light. The shearing interferometer measures the state of divergence and convergence of illumination light with a pattern of interference fringes when an optical glass with both surfaces polished flat and of a thickness of about several mm is inserted obliquely with inclination in the optical path of the illumination light and light reflected on the front surface and light reflected on the back surface are projected on a screen; there is SPUV-25 manufactured by SIGMA KOKI Co., Ltd. or the like. When an image sensor such as a CCD sensor or a CMOS sensor is installed at the screen position, automatic measurement of the state of divergence and convergence of the illumination light can be achieved. The Shack-Hartmann wavefront sensor divides a wavefront with a fine lens array, projects onto an image sensor such as a CCD sensor, and measures the tilts of individual wavefronts from displacements of projection positions. Compared with the shearing interferometer, it can perform detailed wavefront measurement such as partial wavefront disturbance. When it is determined by wavefront measurement that the light incident on the illumination intensity distribution control part 7 is not quasi-collimated light but is diverged or converged, the illumination light can be made closer to quasi-collimated light by displacing the lens group of the beam expander 5 described above in the direction of the optical axis. When it is determined by wavefront measurement that the wavefront of the light incident on the illumination intensity distribution control part 7 is partially tilted, the wavefront can be made closer to a flat one, that is the illumination light can be made closer to quasi-collimated light by inserting a spatial optical phase modulation element 26, which is a sort of SLM, in the preceding stage of the illumination intensity distribution control part 7 as shown in FIG. 15 and providing suitable phase differences at respective positions of the light flux cross section so that the wavefront becomes flat. With the measurement/adjustment means of wavefront accuracy described above, the wavefront accuracy (deviations from a predetermined wavefront (a design value)) of light incident on the illumination intensity distribution control part 7 can be suppressed to $\lambda/10$ rms or less.

An illumination intensity distribution on the sample plane adjusted at the illumination intensity distribution control part 7 is measured with the illumination intensity distribution monitor 24. Incidentally, even when the normal illumination is employed as shown in FIG. 1, an illumination intensity distribution on the sample plane adjusted at the illumination intensity distribution control part $7v$ is similarly measured with the illumination intensity distribution monitor 24. The illumination intensity distribution monitor 24 is to image the sample plane on an image sensor such as a CCD sensor or a CMOS sensor via lenses and to detect it as an image. The image of the illumination intensity distribution detected with the illumination intensity distribution monitor 24 is processed at the control unit 53, the centroid position of the intensity, the maximum intensity, the position of the maximum intensity, the width and the length of the illumination intensity distribution (the width and the length of an area of the illumination intensity distribution having a predetermined intensity or more or having a predetermined ratio or more relative to the maximum intensity value), and the like are calculated out and then displayed on the display unit 54 together with a contour shape, sectional waveforms, and the like of the illumination intensity distribution.

When the oblique incidence illumination is performed, due to height displacement of the sample plane, a displacement of the position of the illumination intensity distribution and disturbance in the illumination intensity distribution with defocusing occur. In order to suppress them, the height of the sample plane is measured and, when the height is off, the deviation is corrected by the illumination intensity distribution control part 7 or height adjustment regarding the Z axis of the stage 103. The height measurement of the sample plane is consisted of a light beam emission part 31 and a light receiving part 32 which receives a light beam emitted from the light beam emission part 31 and scattered and reflected on the sample plane. The light beam emission part 31 comprises a light source such as a semiconductor laser and a projection lens. The light receiving part 32 comprises a light receiving lens and a position sensitive detector. In order to perform measurement of a sample plane with high gloss such as a semiconductor silicon surface or a magnetic disc substrate surface, the light beam emission part 31 and the light receiving part 32 are arranged so that light emitted from the light beam emission part 31 and regularly reflected on the sample plane is detected by the light receiving part 32. The height displacement of the sample plane is detected as a positional shift of the light spot detected by the position sensitive detector of the light receiving part 32 according to the principle of triangulation.

The correction of the positional shift of the illumination light irradiation position in the in-sample-plane direction caused by the height displacement of the sample plane is carried out by adjustment of a deflection angle of a deflection means 33 which is provided downstream of the illumination intensity distribution control part 7 for directing the illumination light toward the sample plane. The deflection means 33 comprises a reflecting mirror which deflects the illumination light and a piezo element which controls an angle with respect to the axis of the illumination light of the reflecting mirror, and controls the angle in a range of about ±1 mrad with a frequency equal to or greater than 400 Hz. An amount of a positional shift of the illumination light irradiation position in the in-sample-plane direction is obtained from the measured value of height displacement and the incidence angle of the illumination light, and the reflecting mirror is controlled as a control signal output from the control unit 53 is received in the deflection means 33 so that the shift is corrected. Incidentally, the positional shift of the illumination light irradiation position in the in-sample-plane direction can also be corrected by directly measuring the centroid position or the like of the illumination intensity distribution using the illumination intensity distribution monitor 24. When the positional shift of the illumination light irradiation position in the in-sample-plane direction caused by the height displacement of the sample plane is corrected by the above-described deflection means 33, the optical path length between the illumination intensity distribution control part 7 and the sample surface deviates from that before correction and, therefore, defocusing of the illumination spot occurs depending on an amount of the shift. An amount of change in the optical path length is obtained from the measured value of height displacement and the incidence angle of the illumination light, and, based on this, the defocusing is mitigated by the positional adjustment of the optical elements comprised in the illumination intensity distribution control part 7 in the direction of the optical axis, the divergence angle adjustment of the beam expander 5, or the like.

Figure 32:
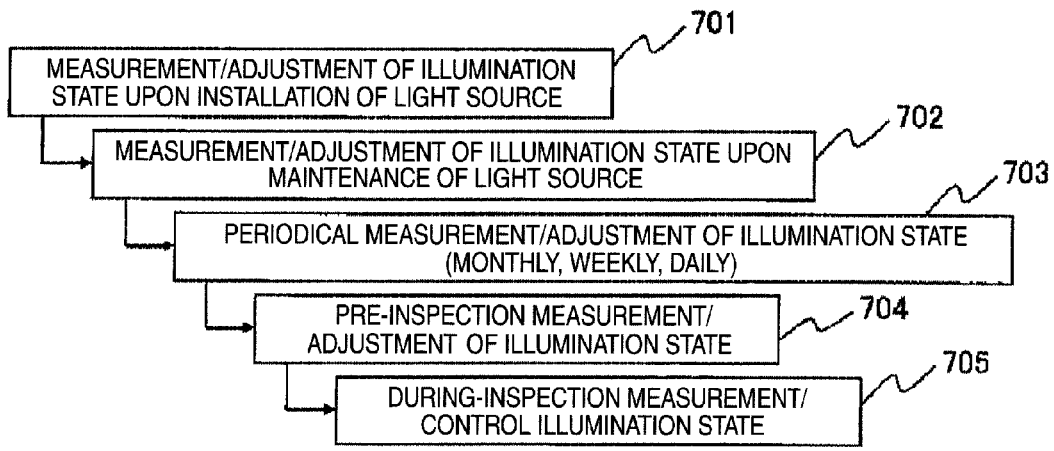
FIG. 32 is a diagram showing a procedure of adjustment of an illumination status in the illumination unit of the defect inspection device according to the present invention.

Explanation is given with reference to FIG. 32 at what time interval and/or timing adjustment of an illumination state is performed in the respective constituent elements of the illumination unit 101. As for measurement/adjustment of an illumination state upon installation of a light source 701, from the upstream of the optical path of the illumination unit 101, adjustments of the attenuator 3, the exit light adjustment part 4, the beam expander 5, the polarization control part 6, the illumination intensity distribution control part 7, and the deflection means 33 are carried out step by step so that the illumination light is adjusted to pass through the illumination intensity distribution control part 7 along a predetermined designed optical path with a predetermined amount of light, a predetermined beam diameter, a predetermined divergence angle, a predetermined wavefront accuracy, and a predetermined polarization state. The measurement/adjustment of an illumination state upon installation of a light source 701 also includes a time when the light source 2 is replaced with a new one of equivalent functions and performance in order to cope with change of a state associated with the life of the light source such as reduction in the output of the light source 2 due to its long-time operation.

Besides, since in a high output laser light source used as the light source 2 a light irradiation position relative to a nonlinear optical crystal in the interior of the light source deteriorates due to long-time use, the light irradiation position relative to the nonlinear optical crystal is displaced (the position of the crystal relative to the optical path is shifted) at constant intervals for lifetime improvement of the light source. There occurs in some cases that the optical path of light emitted from the laser light source would not reproduce before and after this and passing positions or travelling directions of the light may shift. In order to measure/correct the shift and restore the illumination to its original sate, measurement/adjustment of an illumination state upon maintenance of a light source 702 is carried out. In measurement/adjustment of the illumination state upon maintenance of the light source 702, since all of the position, the direction of emission, the divergence angle, and the polarization state of the emitted light can change in the light source 2 which is in the most upstream of the illumination unit 101, the state is measured in all of the beam monitors 22 and 23 and the illumination intensity distribution monitor 24, which are means for the illumination state measurement, and any of the attenuator 3, the exit light adjustment part 4, the beam expander 5, the polarization control part 6, the illumination intensity distribution control part 7, and the deflection means 33 is adjusted as needed. The measurement/adjustment of the illumination state upon maintenance of the light source 702 is carried out at a timing such as after the light irradiation position is shifted relative to the nonlinear optical crystal in the interior of the light source, after cleaning of optical elements in the interior of the light source is performed for the maintenance of the light source, or after a lamp is replaced when a high power lamp light source or a lamp-excited laser light source is used as the light source. It is performed at every several months or hundreds of hours as the time interval.

In order to suppress a change in the illumination state caused by a change in the output of the light source 2 due to time lapse, a change in the installation position or the installation angle of the optical element constituting the illumination unit 101 due to drift, or the like, periodic measurement/adjustment of an illumination state 703 is carried out on a monthly, weekly, or daily basis. The state is measured in all of the beam monitors 22 and 23 and the illumination intensity distribution monitor 24, which are means for the illumination state measurement, and any of the attenuator 3, the exit light adjustment part 4, the beam expander 5, the polarization control part 6, the illumination intensity distribution control part 7, and the deflection means 33 is adjusted as needed.

Pre-inspection measurement/adjustment of an illumination state 704 is performed after it is adjusted in the periodic measurement/adjustment of the illumination state 703 is carried out in order to correct shifts in the positions and the angles of the optical elements due to an environmental change (such as changes in atmospheric pressure and/or temperature) and/or drifts in the illumination unit 101. The pre-inspection measurement/adjustment of the illumination state 704 is more frequent than the periodic measurement/adjustment of the illumination state 703 and, if it requires a long time, time efficiency of the inspection is reduced and a substantial operation time of the inspection device decreases; measurement/adjustment of the illumination state which can be carried out in a short time is performed. More specifically, measurement of an illumination intensity distribution on the sample plane, which is the final output of the illumination unit 101, is carried out by the illumination intensity distribution monitor 24, and the adjustment of the height of the sample plane by the stage 103, the adjustment of the illumination light irradiation position by the deflection means 33, or the adjustment of the positions of the optical elements comprised in the illumination intensity distribution control part 7 is performed.

During-inspection measurement/adjustment of an illumination state 705 is carried out to suppress a change in the illumination intensity distribution due to the height variation of the sample plane by optical/mechanical means in the illumination unit 101 or in the stage 103, or to correct its influence in the detection unit 102 and the signal processing unit 105, which are in subsequent stages. The suppression of a change in the illumination intensity distribution due to the height variation of the sample plane by optical/mechanical means is, as described in explanation of the aforementioned illumination intensity distribution monitor 24, to correct a change in the centroid position of the illumination intensity distribution or a shape change due to defocusing of the illumination intensity distribution, through the adjustments of the deflection part 33, the illumination distribution control part 7, the spatial optical phase modulation element 26, or the stage 103 based on the values measured by the illumination intensity distribution monitor 24 or by the above-mentioned sample plane height measurement means. This correction is carried out on a real-time basis during inspection of the sample plane. The influences of a change of the illumination intensity distribution on the inspection result due to a variation in the height of the sample plane refers to the fact that, when the illumination intensity distribution is not made completely flat, the illumination intensity varies depending on positions where defects pass, which results in a variation in an amount of the scattered light and thus the dimensions of the defects calculated from an amount of the scattered light in the signal processing unit 105 to be explained later, or the defect detection sensitivity varies. The above variations are suppressed by recording measured values of the signal intensity distributions measured with the illumination intensity distribution monitor 24 for each scan position during inspection and, with this, correcting a threshold value or an amplitude of defect signal used in defect detection in the signal processing unit 105 or correcting the values of the defect signal used in the calculation of the defect dimensions.

The during-inspection measurement/adjustment of the illumination state 705 is carried out to correct the influence in the detection unit 102 and the signal processing unit 105, which are in subsequent stages and suppress the change in the illumination intensity distribution due to the height variation of the sample plane by optical/mechanical means in the illumination unit 101 or in the stage 103. In the suppression of the change in the illumination intensity distribution due to the height variation of the sample plane in the illumination unit 101, as described in explanation of the aforementioned the illumination intensity distribution monitor 24, the change in the centroid position of the illumination intensity distribution or the shape change due to defocusing of the illumination intensity distribution is corrected through adjustments of the deflection part 33, the illumination distribution control part 7, the spatial optical phase modulation element 26, or the stage 103 based on of the values measured by the illumination intensity distribution monitor 24 or by the aforementioned sample plane height measurement means. This correction is carried out on a real-time basis during inspection of the sample plane.

Figure 17:
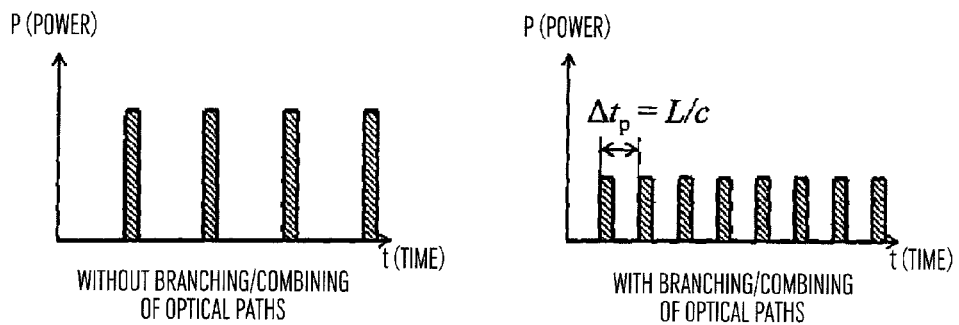
FIG. 17 contains graphs showing a result of reduction of an energy per single pulse with the optical path branching and the optical path combining.

When a pulsed laser, with which a high output can easily be obtained, is used as the light source 2, since the energy of illumination applied to the sample is concentrated at the time moment of incidence of a pulse, there is a case where thermal damage on the sample may occur, which is attributed to instantaneous temperature increase due to incidence of the pulse. To avoid this, it is effective to reduce an energy per pulse while keeping the total energy as shown in FIG. 17 by branching out the optical path of the pulsed laser and combining optical paths after providing a difference in optical paths between the branched optical paths.

Figure 16:
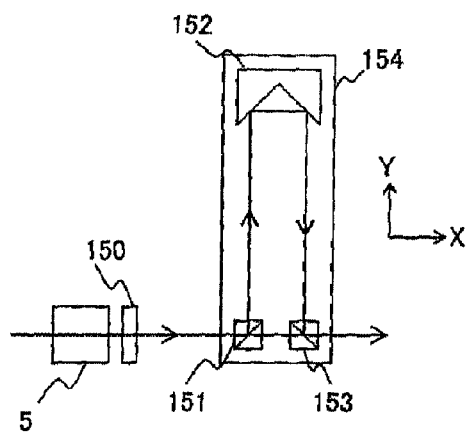
FIG. 16 is a diagram showing an example of a means for reducing an energy per single pulse with optical path branching and optical path combining in the illumination unit of the defect inspection device according to the present invention.

In FIG. 16 an example of an optics system to implement the above. The illumination light after passing through the beam expander 5 is branched out by a polarizing beam splitter 151 into a first optical path reflected by the polarizing beam splitter 151 and a second optical path transmitting through the polarizing beam splitter 151. The first optical path is reflected by a retroreflector 152 to return, reflected by a polarizing beam splitter 153, and combined with the second optical path. The retroreflector 152 comprises two or more reflecting mirrors perpendicular to each other and is to turn back input light to a direction opposed by 180 degrees. In order to make the intensity of light reflected by the polarizing beam splitter 151 and the intensity of light transmitting through equal to each other, the polarization of the illumination light is adjusted by a wave plate 150 to be circularly polarized, linearly polarized of an oblique angle of 45 degrees, or the like. Letting an optical path difference between the first optical path and the second optical path be L, a time interval $\Delta t_p$ between a light pulse passing through the first optical path and a light pulse passing through the second optical path is equal to L/c. By setting $\Delta t_p$ equal to or larger than a time necessary for a temperature increase upon incidence of a single pulse to be relaxed, the instantaneous temperature increase of the sample by a single pulse and the temperature increase caused by heat accumulation due to a plurality of pulses can be suppressed.

In the above optical path combination, when an accuracy of the combination is low and positions or travelling directions of two optical paths are shifted with each other after combination, as the illumination light input to the illumination intensity distribution control part 7 deviates from its ideal state (a quasi-collimated Gaussian beam in the present embodiment), a problem occurs that the state of the illumination intensity distribution formed on the sample surface eventually deviates from its desired state. The longer the optical path difference between the two optical paths is in order to secure the aforementioned time interval of pulses $\Delta t_p$, more easily the problem tends to occur. The smaller the beam diameter of a light flux is, the greater the influence of the positional shift (the shift of the intensity distribution after combination from the Gaussian beam) between light fluxes of the two optical paths is; therefore, in the present embodiment, the influence of the shift of the optical path positions is mitigated by performing optical path division and combination at a later stage of the beam expander 5 to branch out and combine the optical paths after expansion of the beam diameter. Turning back of the first optical path is possible even using two mutually independent mirrors; in such a case, however, since a deviation of angles between the two light fluxes to be combined arises when a relative angular deviation between the two mirrors is created, a configuration using the retroreflector 152, with which such a problem will not rise, is adopted. Also, the illumination unit 101 including the optics system shown in FIG. 16 is installed on an optical bench made of aluminum or the like and, when the position of the retroreflector 152 is displaced in the X direction of FIG. 16 with respect to the light flux input to the retroreflector 152 due to a reason such as a distortion of the optical bench by environmental changes like a temperature change, there exists a problem such that the position of the light flux reflected by the retroreflector 152 and turning back to the polarizing beam splitter 153 is displaced in the X direction to cause a shift of the position. Therefore, by installing the polarization beam splitters 151 and 153 and the retroreflector 152 on a surface plate 154 mounted on the optical bench which supports the illumination unit 101 thereon, the relative positional relationship can be maintained without being influenced by a distortion caused by an arrangement or a shape of the entire optical bench which supports the illumination unit 101 thereon or the like. Further, use of a low-expansion material such as glass ceramic as for the surface plate 154 is also effective to suppress distortion caused by temperature change. Using the low-expansion material only for the surface plate 154 yields an advantageous effect of being feasible inexpensively compared with doing so for the entire optical bench which supports the illumination unit 101 thereon.

Figure 19:
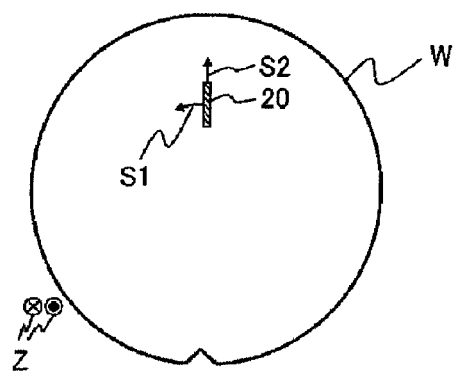
FIG. 19 is a diagram showing a shape of an illumination distribution on a surface of a sample and a scan direction according to the present invention.

An illumination distribution profile (an illumination spot 20) formed on a sample plane by the illumination unit 101 and a method for scanning the sample are explained with reference to FIGS. 19 and 20. A circular semiconductor silicon wafer is assumed as the sample W. The stage 103 comprises a translational stage, a rotary stage, and a Z stage for adjusting the height of the sample plane (none of which is illustrated). The illumination spot 20 has an illumination intensity distribution elongated in one direction as mentioned above; it is supposed that the direction is S2 and the direction substantially perpendicular to S2 is S1. It is scanned in a circumferential direction S1 of a circle having the rotation axis of the rotary stage at its center due to the rotational movement of the rotary stage and in a translational direction S2 of the translational stage due to the translational movement of the translational stage, respectively. By scanning in the scan direction S2 by a distance equal to or less than the length of the illumination spot 20 in the longitudinal direction while rotating the sample for one turn by scanning in the scan direction S1, the illumination spot draws a spiral locus T on the sample W and thus the entire surface of the sample 1 is scanned.

Explanation is now given to estimation of an illumination power which can be irradiated without exerting thermal damage to the sample. According to "RE-ZA PUROSESU GIJUTSU HANDOBUKKU" (Laser Processing Technique Handbook) (1992, Asakura Shoten), a temperature increase at a position (x, y, z) when a rectangular uniform illumination intensity distribution is irradiated on a semi-infinite surface is expressed as follows.

$$T(x, y, z, t) = \frac{\varepsilon P \sqrt{\kappa}}{16\sqrt{\pi}\, abK} \int_0^t \frac{1}{\sqrt{\tau}} \left( \mathrm{erf}\frac{x+a}{2\sqrt{\kappa\tau}} - \mathrm{erf}\frac{x-a}{2\sqrt{\kappa\tau}} \right) \times \left( \mathrm{erf}\frac{y+b}{2\sqrt{\kappa\tau}} - \mathrm{erf}\frac{y-b}{2\sqrt{\kappa\tau}} \right) \exp\left(-\frac{z^2}{4\kappa\tau}\right) d\tau \quad \text{[MATH. 1]}$$

Here, ε denotes an illumination absorptance on a surface, P denotes a laser power, κ denotes a thermal diffusivity, K denotes a thermal conductivity, a and b denote halves of a width and a length of an illumination, respectively, and erf denotes the error function. x, y, and z are coordinates with an origin at the center of the rectangular illumination distribution, and z corresponds to the depth direction of a semi-infinite body. The thermal diffusivity κ is obtained from the thermal conductivity K, a density ρ, and a specific heat c with a relationship, κ=K/(ρc). According to MATH. 1, a temperature increase at the center of the rectangular illumination distribution is expressed as follows.

$$T(0, 0, 0, t) = \frac{\varepsilon P \sqrt{\kappa}}{4\sqrt{\pi} \, abK} \int_0^t \frac{1}{\sqrt{\tau}} \text{erf} \frac{a}{2\sqrt{\kappa\tau}} \text{erf} \frac{b}{2\sqrt{\kappa\tau}} d\tau \quad [\text{MATH. 2}]$$

Further, a steady-state value of the temperature increase when it is irradiated for a long time is expressed as follows.

$$T(0, 0, 0, \infty) = \frac{\varepsilon P}{2\pi abK}\left(a\sinh^{-1}\frac{b}{a} + b\sinh^{-1}\frac{a}{b}\right) \quad [\text{MATH. 3}]$$

Figure 20:
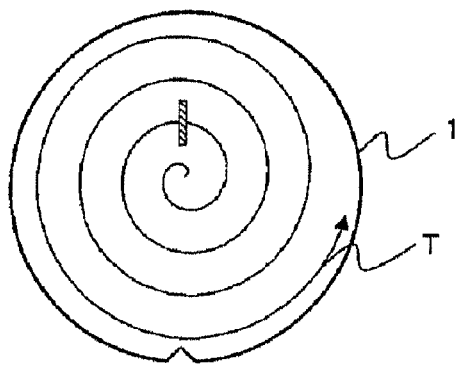
FIG. 20 is a diagram showing a locus of an illumination spot by scanning.

In the case of spiral scanning as shown in FIG. 20, since an effective scan speed approaches to zero at a center part of the sample plane, the illumination light is irradiated for a long time. Therefore, an temperature increase at the center part becomes maximum in the entire sample plane and the value of the temperature increase is obtained using MATH. 3.

Figure 28:
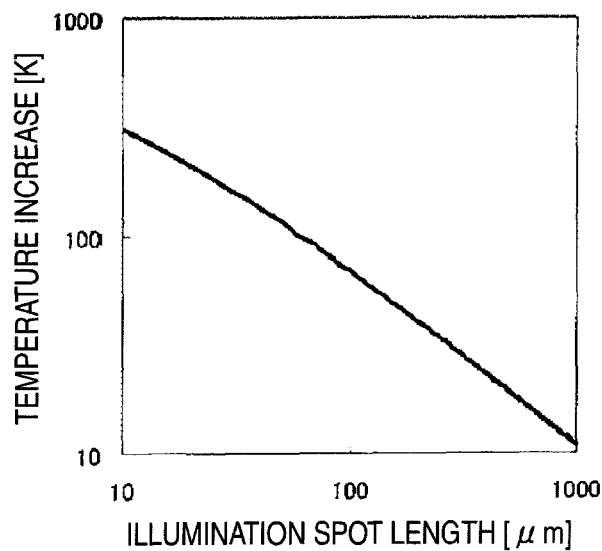
FIG. 28 is a graph showing a relationship between the length of an illumination spot and an increase of temperature on a surface of a sample.
Figure 29:
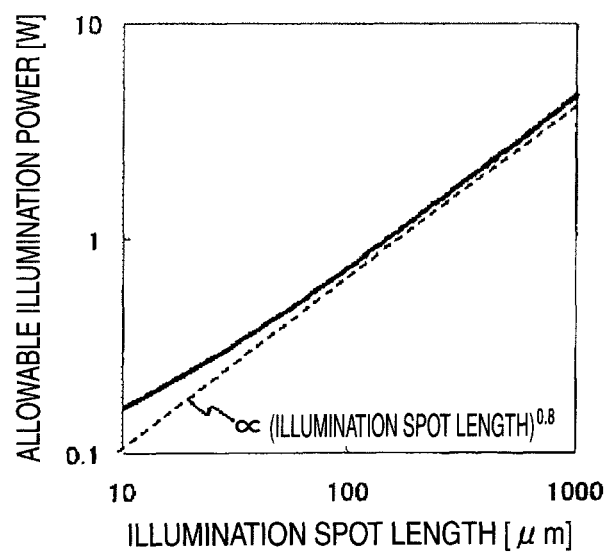
FIG. 29 is a graph showing a relationship between the length of an illumination spot and an allowable illumination power.

Taking a sample of a case when the sample W is a semiconductor silicon wafer, results of obtained temperature increases at the center part of the sample are shown in FIGS. 28 and 29. Based on physical properties and reflectivity of crystalline silicon, it is supposed that ε=0.912, κ=0.000100 [m^2/s], and K=168 [W/mK]. As illumination conditions it is supposed that P=1 [W] and a short side width of the illumination spot 2a=10 [µm], and calculated values of temperature increase with a long side length of the illumination spot 2b in a range of 10 to 1000 [µm] are shown in FIG. 28. Here, supposedly an allowable value of the temperature increase Tc is set, and results of an obtained illumination power Pc (an allowable laser power) when the temperature increase does not exceed Tc are shown in FIG. 29. Here, with an aim of not exceeding a glass transition temperature of 100° C. at which the deformation of polystyrene takes place while it is a material of polystyrene particles generally used as a standard sample in foreign object inspections of semiconductor silicon wafers, it is set that Tc=50 [K] (with which a silicon surface temperature rises up to 75° C. when a room temperature of 25° C. is assumed). From FIG. 29 it can be said that there is a relationship with which the allowable illumination power is to be proportional to about 0.8 of the illumination spot length. Since the value of the temperature increase is proportional to the laser power, this relationship does not depend on the constant value set for Tc.

From the relationship described above between the allowable illumination power and the illumination spot length, when it is confirmed that an illumination power P1 is the upper limit of the illumination power which would not cause damage to the sample even at the center part of the sample with an illumination spot length L1, in other inspection conditions, for example, in conditions that the illumination spot length is set to be 2×L1 to double the inspection rate, the upper limit value of the illumination power is found to be (2^0.8)×P1=1.74×P1. In this manner, by using the relationship between the illumination spot length and the allowable illumination power, optimum illumination conditions for obtaining a maximum amount of scattered light without giving any damage to the sample can easily be calculated and set.

Figure 30:
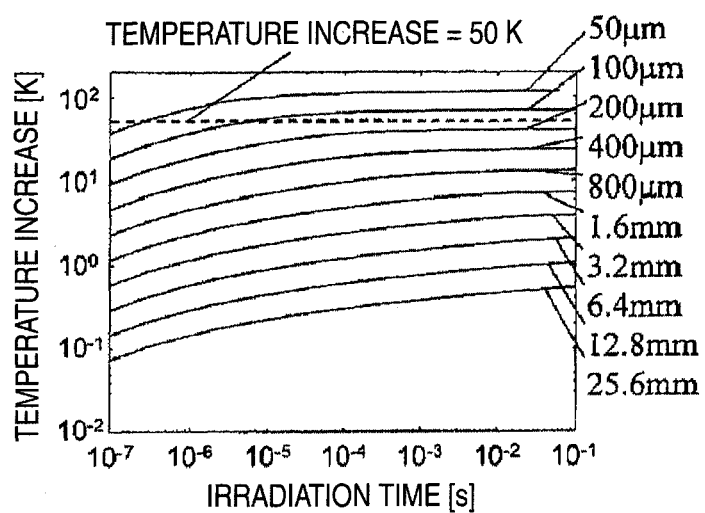
FIG. 30 is a graph showing a relationship between an illumination irradiation time and an increase of temperature on a surface of a sample.
Figure 31:
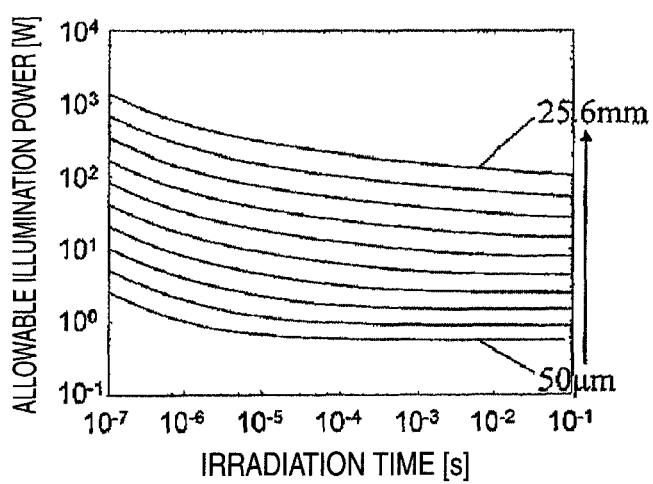
FIG. 31 is a graph showing a relationship between an illumination irradiation time and an allowable illumination power.

In FIGS. 30 and 31 relationships between the illumination light irradiation time and the temperature increase of the semiconductor silicon wafer found using MATH. 1 are shown with different illumination spot lengths of the illumination light. They are calculated assuming that the length of the short side of the illumination spot is 10 µm. In FIG. 31 an allowable illumination power with respect to the irradiation time obtained from the results of FIG. 30 is shown. The irradiation time is determined by the illumination spot short side length and the illumination spot scan speed and, when spiral scanning is carried out with a constant rotational speed, it varies inversely proportional to a distance of the illumination spot position from the center of rotation. By using calculated values shown in FIG. 31, upper limits of the allowable illumination power at every radial positions can be obtained in arbitrary illumination conditions. And by controlling the illumination power using the attenuator 3 in the illumination unit 101 in accordance with the illumination spot scan speed based on these, a maximum amount of scattered light can be obtained without causing any damage to the sample.

Figure 21:
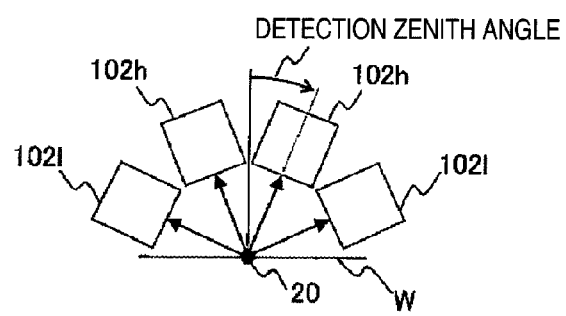
FIG. 21 is a diagram when an arrangement of detection units and detection directions of the defect inspection device according to the present invention are viewed from a side.
Figure 22:
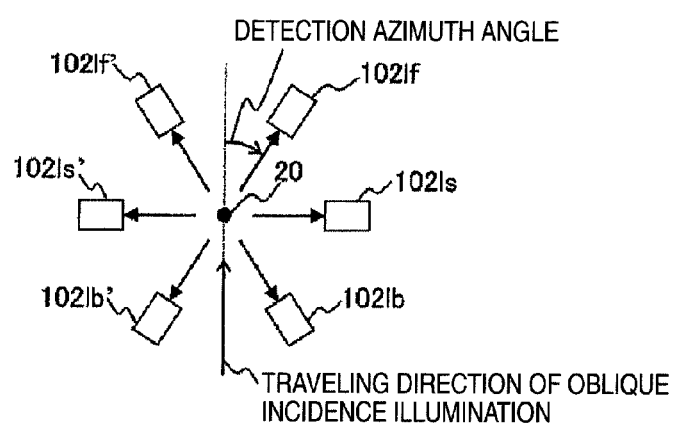
FIG. 22 is a diagram when an arrangement of low-angle detection units and detection directions of the defect inspection device according to the present invention are viewed from the top.
Figure 23:
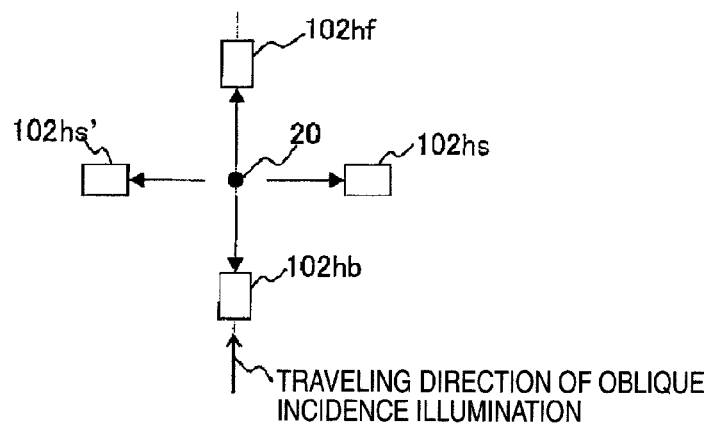
FIG. 23 is a diagram when an arrangement of high-angle detection units and detection directions of the defect inspection device according to the present invention are viewed from the top.

A plurality of detection units 102 are arranged so as to detect scattered light of a plurality of directions emitted from the illumination spot 20. An example of a layout of the detection units 102 with respect to the sample W and the illumination spot 20 is explained with reference to FIGS. 21 to 23. A side view of the layout of the detection units 102 is shown in FIG. 21. An angle formed by a detection direction by a detection unit 102 (a direction of the center of the detection aperture) with respect to a normal to the sample W is defined as a detection zenith angle. The detection units 102 are constituted properly using a high-angle detection part 102*h* with a detection zenith angle of 45 degrees or less and a low-angle detection part 102*l* with a detection zenith angle of 45 degrees or more. Each of the high-angle detection part 102*h* and the low-angle detection part 102*l* comprises a plurality of detector parts so as to cover scattered light scattering in multiple directions at each of the detection zenith angles. A plan view of the layout of the low-angle detection part 102*l* is shown in FIG. 22. An angle formed by the travelling direction of the oblique incidence illumination and the detection direction in a plane parallel to the surface of the sample W is defined as a detection azimuth angle. The low-angle detection part 102*l* properly comprises a low-angle front detection part 102*lf*, a low-angle side detection part 102*ls*, a low-angle back detection part 102*lb*, and those located at positions symmetrical to these with respect to the incidence plane of illumination: a low-angle front detection part 102*lf'*, a low-angle side detection part 102*ls'*, and a low-angle back detection part 102*lb'*. For example, the low-angle front detection part 102*lf* is located at a detection zenith angle of 0 degrees or more and 60 degrees or less, the low-angle side detection part 102*ls* is at a detection zenith angle of 60 degrees or more and 120 degrees ore less, and the low-angle back detection part 102*lb* is at a detection zenith angle of 120 degrees or more and 180 degrees or less. A plan view of the layout of the high-angle detection part 102*h* is shown in FIG. 23. The high-angle detection part 102*h* properly comprises a high-angle front detection part 102*hf*, a high-angle side detection part 102*hs*, a high-angle back detection part 102*hb*, and a high-angle side detection part 102*hs'* located at a position symmetrical to the high-angle side detection part 102*hs* with respect to the incidence plane of illumination. For example, the high-angle front detection part 102*hf* is located at a detection zenith angle of 0 degrees or more and 45 degrees or less, the high-angle side detection part 102*hs* is at a detection zenith angle of 45 degrees or more and 135 degrees or less, and the high-angle back detection part 102*hb* is at a detection zenith angle of 135 degrees or more and 180 degrees or less. Incidentally, although a case where the high-angle detection part 102*h* has four detection parts and the low-angle detection part 102*l* has six detection parts is shown here, it is not limited thereto and the number and the locations of detection parts may properly be varied.

Figure 24:
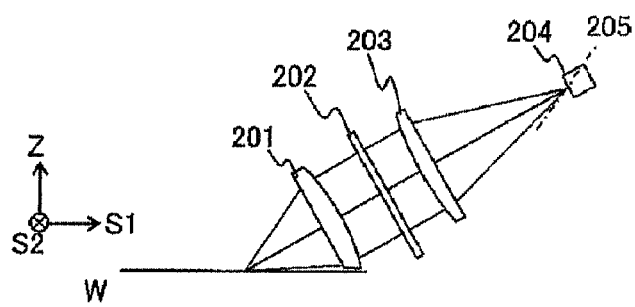
FIG. 24 is a diagram showing an example of a configuration of a detection unit of the defect inspection device according to the present invention.
Figure 25:
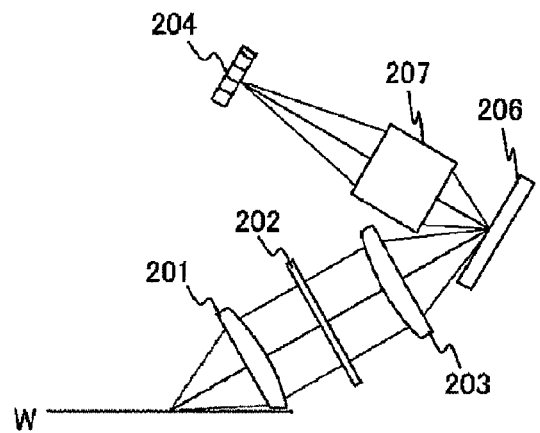
FIG. 25 is a diagram showing a modified example of the configuration of the detection unit of the defect inspection device according to the present invention.

Detailed constructions of the detection unit 102 are shown in FIGS. 24 and 25. A construction of the low-angle and high-angle side detection parts 102*ls* and 102*hs* at the detection zenith angle of 90 degrees is shown in FIG. 24. After scattered light generated from the illumination spot 20 is concentrated by an objective lens 201 and transmitted through a polarizing filter 202, it is guided by an imaging lens 203 onto the light receiving surface of a multi-pixel sensor 204 and detected. In order to efficiently detect the scattered light, a detection NA of the objective lens 201 is preferably equal to or greater than 0.3. In the case of the low-angle detection part, the lower edge of the objective lens is cut off as needed in order for the lower edge of the objective lens not to interfere with the sample plane W. The polarizing filter 202 comprises a polarizing plate or a polarizing beam splitter and is provided to cut a component of linear polarization in an arbitrary direction. As the polarizing plate, a wire-grid polarizing plate with a transmittance equal to or greater than 80% or the like is used. When a component of an arbitrary polarization including elliptical polarization is cut, a polarizing filter 202 comprising a wave plate and a polarizing plate is provided.

The multi-pixel sensor 204 is one with a plurality of light detection pixels arranged in a linear form. Those of high quantum efficiencies (30% or higher) and capable of electrically amplifying electrons after photoelectric conversion in order to perform high sensitivity detection, those with a plurality of light detection pixels capable of reading out their signals in parallel for increase in speed, those capable of easily changing a detection sensitivity (a gain of electrical amplification) by an electric means or the like in a short time to secure a dynamic range of detection, or the like is preferable. As photo detectors which satisfy these, a multi-anode photomultiplier tube, an avalanche photo-diode array, a linear EMCCD (Electron Multiplying CCD) which is capable of parallel read-out of signals, or a linear EBCCD (Electron Bombardment CCD) which is capable of parallel read-out of signals is used. In the present embodiment a construction using a multi-anode photomultiplier tube is explained. An image of the sample plane is focused on a conjugate plane of the sample plane 205 by the objective lens 201 and the imaging lens 203. Since the image is focused obliquely with respect to the sample plane, in terms of the scan direction S1, an object located at a position of a large imaged height is not focused into an image but blurred on the light receiving surface of the multi-pixel sensor 204; however, since the dimension of the illumination spot 20 is small in the scan direction S1, the object located at the position of the large imaged height would not influence on detection.

An example of constructions of the low-angle and high-angle front and back detection parts 102*lf*, 102*hf*, 102*lb*, and 102*hb* is shown in FIG. 25. After scattered light generated from the illumination spot 20 is concentrated by an objective lens 201 and transmitted through a polarizing filter 202, an image (an intermediate image) of the sample plane is focused by an imaging lens 203 on a diffraction grating 206 installed on a conjugate plane of the sample plane. The image of the sample plane formed on the diffraction grating 206 is projected by an imaging system 207 onto the light receiving surface of the multi-pixel sensor 204. The multi-pixel sensor 204 is installed in the conjugate plane of the sample plane aligned with the shape of the illumination spot 20, which is elongated in one direction, so that the array direction of the pixels coincides with a longitudinal direction of the image of the illumination spot 20. As for the diffraction grating 206, in order to diffract light guided by the imaging lens 203 to form the intermediate image in a direction normal to the surface of the diffraction grating 206, one on which a pattern of the diffraction grating is formed is used so that the Nth-order diffracted light of the incident light along the optical axis of the light which is guided by the imaging lens 203 to form the intermediate image is directed in the direction normal to the surface of the diffraction grating 206. In order to increase a diffraction efficiency, a blazed diffraction grating is used. By adopting the above construction and installing a multi-pixel sensor 204 in a plane conjugate to the sample plane, an effective field of view can be secured in a wide range by suppressing out-of-focus even with respect to the S1 direction on the sample plane and scattered light can be detected with a small loss in an amount of light.

Incidentally, when an illumination power is controlled according to the scan speed of the illumination spot based on the aforementioned calculated values shown in FIG. 31, a peak value in a signal of the scattered light varies even for defects of the same dimension. By controlling an applied voltage, which determines a multiplication gain of the multi-pixel sensor 204 of the detection unit 102 in parallel to control of the illumination power, the dynamic range of the multi-pixel sensor 204 is dynamically adjusted according to the control of the illumination power. The control of the applied voltage is carried out so that the multiplication gain of the multi-pixel sensor 204 is inversely proportional to the illumination power given for each scan speed of the illumination spot.

Here, relationships among the length of the illumination spot 20, the optical magnification of the detection unit 102, and the dimensions of the multi-pixel sensor 204 are explained. When high-speed inspection with a high sensitivity is carried out, the length of the illumination spot 20 is set at about 400 μm. When one with 32 pixels arranged with a pitch of 1 mm is used as the multi-pixel sensor 204, the optical magnification of the detection unit becomes 80 and the pitch of the pixels projected on the sample plane becomes 12.5 μm. At these conditions, when the sample is rotated at a rotational speed of 2,000 rpm, a circular sample of a diameter of 300 mm is scanned in 11 seconds and a circular sample of a diameter of 450 mm is in 17 seconds for the entire surface thereof. When inspection is performed at even higher speed, the length of the illumination spot 20 is set at about 1,000 μm. When one with 32 pixels arranged with a pitch of 1 mm is used as the multi-pixel sensor 204, the optical magnification of the detection unit becomes 32 and the pitch of the pixels projected on the sample plane becomes 31.3 μm. At these conditions, when the sample is rotated at a rotational speed of 2,000 rpm, a circular sample of a diameter of 300 mm is scanned in 5 seconds and a circular sample of a diameter of 450 mm is in 7 seconds for the entire surface thereof.

Figure 26:
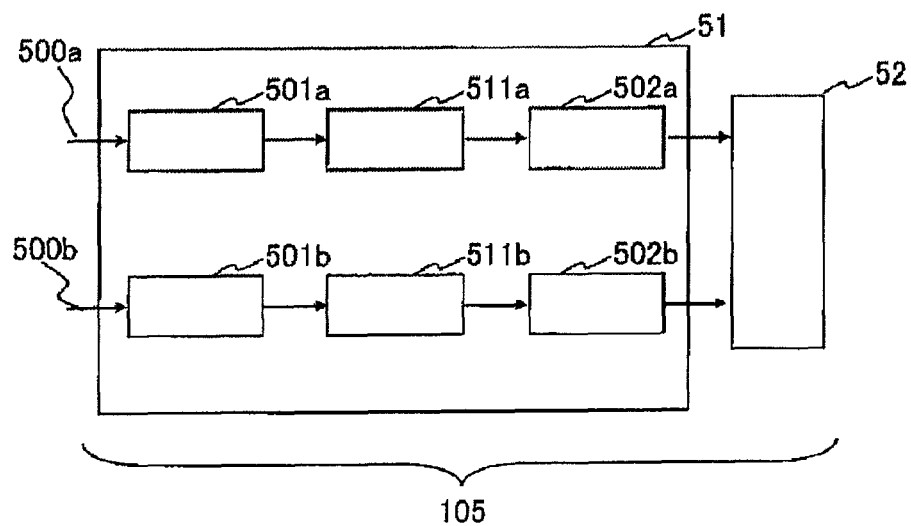
FIG. 26 is a diagram showing a configuration of an analog processing unit of the defect inspection device according to the present invention.
Figure 27:
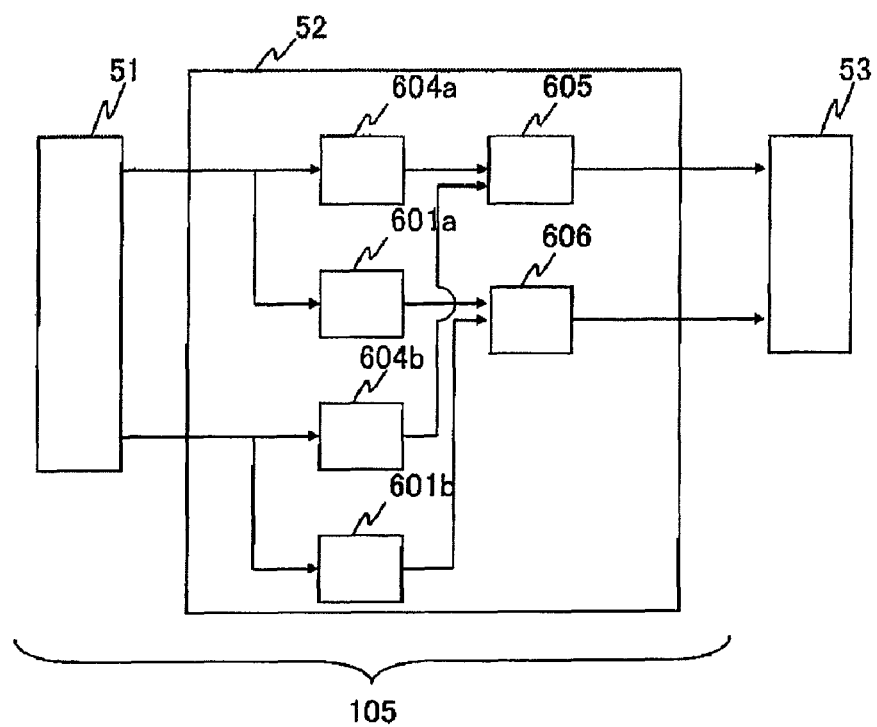
FIG. 27 is a diagram showing a configuration of a digital processing unit of the defect inspection device according to the present invention.

Next, with reference to FIGS. 26 and 27, the signal processing unit 105 is explained which performs at a high accuracy classification of various defect types and/or estimation of defect dimensions based on detection signals of intensities of scattered light in various directions simultaneously detected by a plurality of detection optics systems which cover a wide range of angles. The signal processing unit 105 is constructed comprising an analog processing part 51 and a digital processing part 52.

Explanation is first given to the analog processing part 51 constructing the signal processing unit 105 using FIG. 26. Here, for simplicity, explanation is provided to a structure of the analog processing part 51 when two systems of the detection units 102a and 102b (not shown) are comprised out of a plurality of the detection units 102. Signal currents 500a and 500b output from detectors comprised in the detection units 102a and 102b, respectively, are converted to voltages and then amplified by preamplifier parts 501a and 501b, respectively. The amplified analog signals are cut in their high frequency noise components by low pass filters 511a and 511b, and then converted to digital signals by analog/digital conversion parts (A/D conversion parts) 502a and 502b which has sampling rates higher than the cut-off frequencies of the low pass filters 511a and 511b, and output therefrom.

Then, explanation is given to the digital processing part 52 constructing the signal processing unit 105 using FIG. 27. As for respective output signals from the analog processing part 51, in the digital processing part 52, respective defect signals 603a and 603b are extracted by high pass filters 604a and 604b and are input to a defect determination part 605. Since a defect is scanned in the S1 direction with the field of illumination 20, the waveform of the defect signal corresponds to an expansion/contraction of an illumination distribution profile of the field of illumination 20 in the S1 direction. Accordingly, by letting frequency bands including the defect signal waveforms pass through and cutting frequency bands including relatively more noise and DC components thereof by the respective high pass filters 604a and 604b, S/N ratios of the defect signals 603a and 603b are improved. As the respective high pass filters 604a and 604b, high pass filters or band pass filters having specific cut-off frequencies and designed to cut off components of the frequencies or higher, or FIR filters which have similar shapes to the waveforms of the defect signals reflecting the shape of the illumination spot 20 are used. The defect determination part 605 performs threshold-processing on inputs of signals including defect waveforms output from the respective high pass filters 604a and 604b and determines presence or absence of a defect. Namely, since defect signals based on the detection signals from the plurality of the detection optics systems are input to the defect determination part 605, the defect determination part 605 can carry out high-sensitivity defect inspection compared with defect detection based on a single defect signal by performing threshold-processing on a sum of a plurality of defect signals or on a weighted average thereof, or by performing logical OR and/or AND operations in the same coordinate system set for the surface of the wafer with respect to a group of defects extracted by performing threshold-processing on the plurality of the defect signals.

Further, for a location at which a defect is determined to be present, the defect determination part 605 provides the control unit 53 with estimated values of defect coordinates indicating a position of the defect in the wafer and defect dimensions calculated based on its defect waveform and sensitivity information signal as defect information to output to the display unit 54 or the like. The defect coordinates are calculated with a basis of the centroid of the defect waveform. The defect dimensions are calculated based on an integrated value or a maximum value of the defect waveform.

Besides, the respective output signals from the analog processing part 51 are input to low pass filters 601a and 601b, respectively, in addition to the high pass filters 604a and 604b which construct the digital processing part 52, and at the respective low pass filters 601a and 601b low frequency components and DC components corresponding to an amount of scattered light (a haze) from fine roughness in the illumination spot 20 on the wafer are output. In this way, the outputs from the respective low pass filters 601a and 601b are input to a haze processing part 606 to perform processing of haze information therein. That is, the haze processing part 606 outputs a signal corresponding to the magnitude of the haze at each location on the wafer as a haze signal according to the magnitudes of he input signals obtained from the respective low pass filters 601a and 601b. Also, since an angular distribution of an amount of the scattered light from roughness changes according to a spatial frequency distribution of fine roughness, by inputting haze signals from respective detectors in the plurality of the detection units 102 installed at direction and angles different from each other as shown in FIGS. 21 to 23 to the haze processing part 606, information regarding the spatial frequency distribution of fine roughness can be obtained from their intensity ratios in the haze processing part 606.

Figure 8:
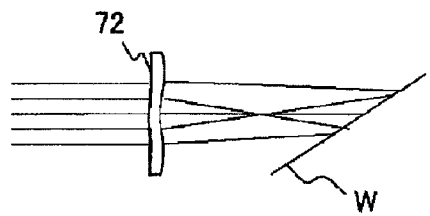
FIG. 8 is a diagram showing a modified example of an optical element comprised in the illumination intensity distribution control part of the defect inspection device according to the present invention.
Figure 9:
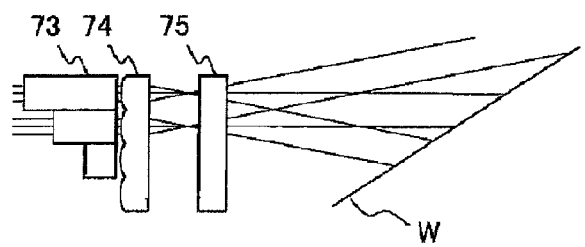
FIG. 9 is a diagram showing a modified example of optical elements comprised in the illumination intensity distribution control part of the defect inspection device according to the present invention.
Figure 10:
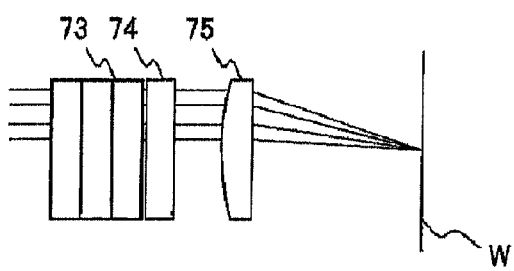
FIG. 10 is a diagram showing a modified example of optical elements comprised in the illumination intensity distribution control part of the defect inspection device according to the present invention.
Figure 11:
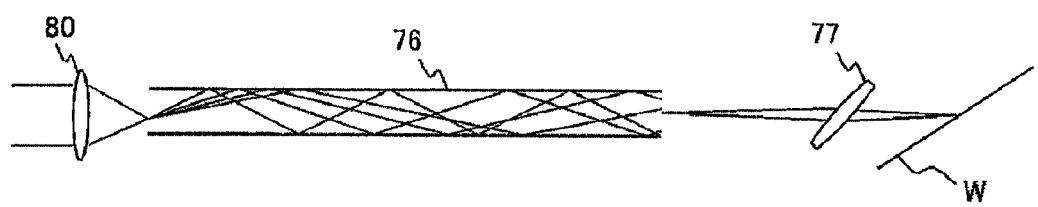
FIG. 11 is a diagram showing a modified example of optical elements comprised in the illumination intensity distribution control part of the defect inspection device according to the present invention.
Figure 12:
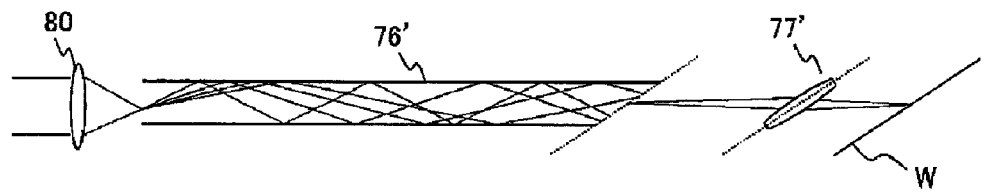
FIG. 12 is a diagram showing a modified example of optical elements comprised in the illumination intensity distribution control part of the defect inspection device according to the present invention.
Figure 13:
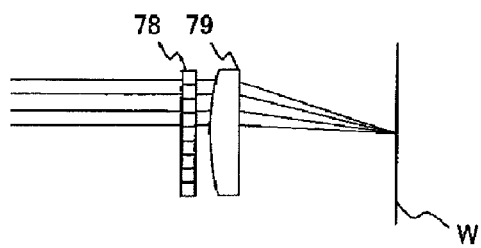
FIG. 13 is a diagram showing a modified example of optical elements comprised in the illumination intensity distribution control part of the defect inspection device according to the present invention.

Explanation is now given on a modified example of the optical elements used in the illumination intensity distribution control part 7. As alternate optical elements having a function similar to that of the diffractive optical element 71, an aspherical lens 72 (FIG. 8), a combination of a cylindrical lens array 74 and a cylindrical lens 75 (FIGS. 9 and 10), a combination of a light pipe 76 and an imaging lens 77 (FIGS. 11 and 12), or a spatial light modulator (SLM: Spatial Light Modulator) 78 (FIG. 13) is used. As shown in FIG. 9, the cylindrical lens array 74 plays a role of separating the incident collimated light fluxes into a plurality of collimated light fluxes and bending respectively in the incident plane of illumination for the sample plane, and overlapping them while shifting their positions on the sample plane. When a laser light source is used as the light source 2 and a plurality of illumination fluxes are overlapped with each other on the sample plane, speckles are generated and the uniformity of the illumination intensity distribution decreases. To avoid this, optical path differences longer than a coherence distance of the light source are provided to a plurality of illumination light fluxes by an optical path difference supply means such as a stepwise quartz glass block. As shown in FIG. 10, in the incident plane of illumination for the sample plane, incident light fluxes are transmitted through the cylindrical lens array 74 while remaining as collimated light and then focused on the sample plane by the cylindrical lens 75. The light pipe 76 is a cylindrical or polygonal pillar tube, the inner walls of which is made of a material such as a metal which reflects illumination light thereon with a high reflectivity and the interior of which is hollow or filled with a material which transmits the illumination light with a high transmittance. Light concentrated near an inlet of the light pipe 76 by a condensing lens 80 at a preceding stage of the light pipe 76 repeats reflection many times while passing through the interior of the light pipe 76 to yield a spatially uniform intensity distribution at an outlet of the light pipe 76. With the imaging lens 77 the outlet of the light pipe 76 and the sample surface are connected in a conjugate relationship so that a light intensity distribution similar to a uniform light intensity distribution at the outlet of the light pipe 76 is formed on the sample plane. By tilting the imaging lens 77 with respect to the outlet plane and the optical axis of the light pipe 76 as in FIG. 11, an image of a uniform illumination intensity distribution can be focused on the sample plane W. Or by using such a light pipe 76' that an outlet plane is processed to be parallel to the sample plane W as in FIG. 12, an optical path distance between the outlet plane of the light pipe and the sample plane becomes the same regardless of the imaged height, and thus designing an imaging lens 77' becomes easy. The spatial light modulator 78 controls an illumination intensity distribution on the sample plane by modulating an intensity or a phase in each minute area in a cross section of the incident light flux and it is possible to dynamically control the illumination intensity distribution on the sample plane as receiving a control signal emitted from the control unit 53. As the spatial light modulator 78, a liquid crystal element, a magneto-optic spatial light modulator, a digital micro-mirror device (a reflection type), or the like is used. With the spatial light modulator 78 alone or a combination of the spatial light modulator 78 and a condensing lens 79 a desired illumination intensity distribution is formed.

Figure 33:
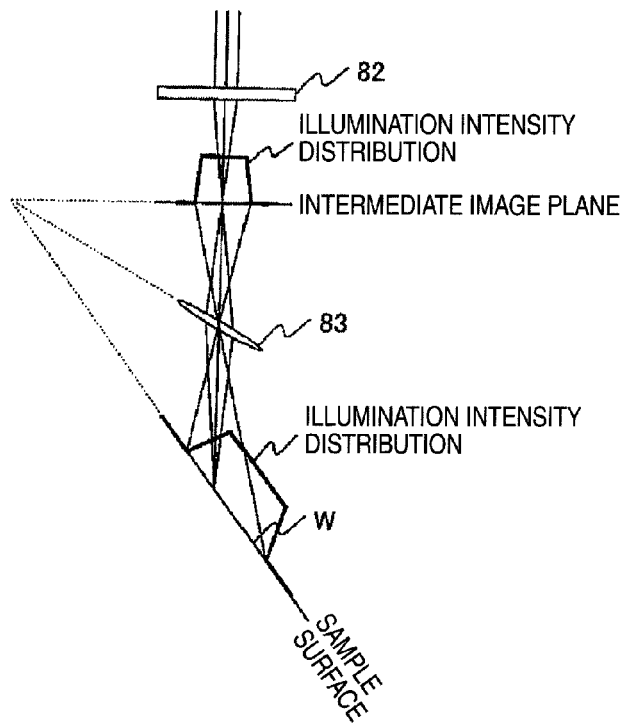
FIG. 33 is a diagram showing an eighth example of optical elements comprised in the illumination intensity distribution control part of the defect inspection device according to the present invention.

In FIG. 33 a construction of a modified example of the illumination intensity distribution control part 7 is shown which forms a predetermined illumination intensity distribution on an intermediate image plane by an illumination intensity distribution forming element 82 such as a diffractive optical element and transcribes it onto the sample surface which is in a conjugate relationship with the intermediate image plane via an imaging system 83. The illumination intensity distribution forming element 82 comprises a diffractive optical element and/or an aspherical lens and forms an illumination intensity distribution of a uniform intensity in one direction. The intermediate image is relayed on the sample surface by the imaging system 83 and is focused thereon. A relationship among the intermediate image plane, the lens plane of the imaging system 83, and the sample surface follows a relationship of Scheimpflug. Namely, they intersect on one axis in space (at one point in FIG. 33). In order to suppress an aberration due to off-axis light and an aberration due to inclination of the sample plane, the imaging system 83 is constructed with a plurality of lenses or aspherical lenses.

Figure 34:
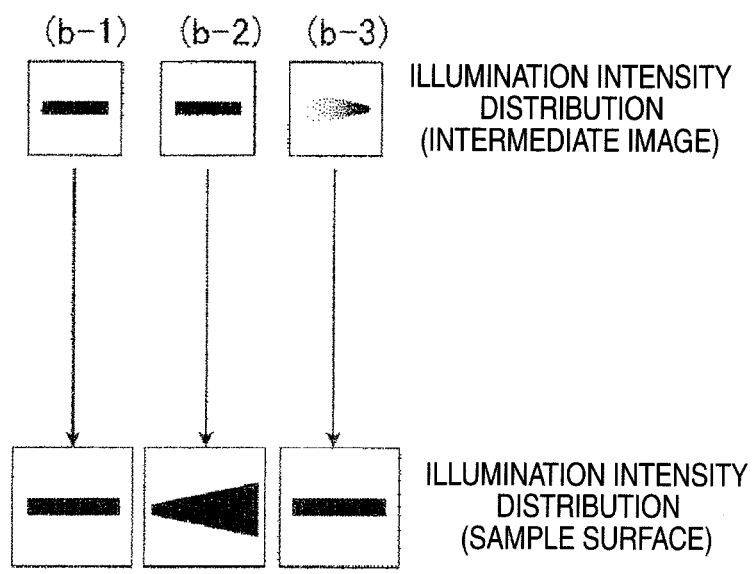
FIG. 34 is diagrams showing intermediate images of illumination intensity distributions and illumination intensity distributions on the surface of the sample with the illumination intensity distribution control part of the modified example of the defect inspection device according to the present invention.

When the intermediate image of the illumination intensity distribution is focused on the sample surface tilted with respect to the intermediate image plane in the construction of FIG. 33, since an imaging magnification varies according to the imaged height (at positions on the sample surface), the rectangular intermediate image is deformed into a trapezoidal shape as shown in (b-2) of FIG. 34. In order to mitigate this influence, the illumination intensity distribution forming element 82 is designed in advance so that an illumination intensity distribution on the intermediate image plane becomes a trapezoidal shape which is in a reversed direction to the trapezoidal shape of (b-2) of FIG. 34, and it is imaged on the sample surface so that a rectangular illumination intensity distribution can be formed on the sample surface as shown in (b-3) of FIG. 34. Here, by further forming such an illumination intensity distribution as to be proportional to the imaging magnification for each imaged height on the intermediate image plane, the illumination intensity distribution on the sample surface can be made uniform. Moreover, a phenomenon that the rectangular intermediate image mentioned above is deformed into a trapezoid takes place when the angle of view of the imaging system 83 is relatively large; thus, by adopting a construction which makes the angle of view small, the influence can be mitigated ((b-1) of FIG. 34). Specifically, it is good if a size of the field of view is small with respect to the work distance or a focal length of the imaging system 83 such that a ratio of the field of view to the work distance or the focal length is equal to or less than 100:1 or the angle of view is equal to or less than 10 mrad. For example, when the length of the illumination intensity distribution in the longitudinal direction is 1 mm, it is good if the work distance of the imaging system 83 is 100 mm or longer.

Figure 35:
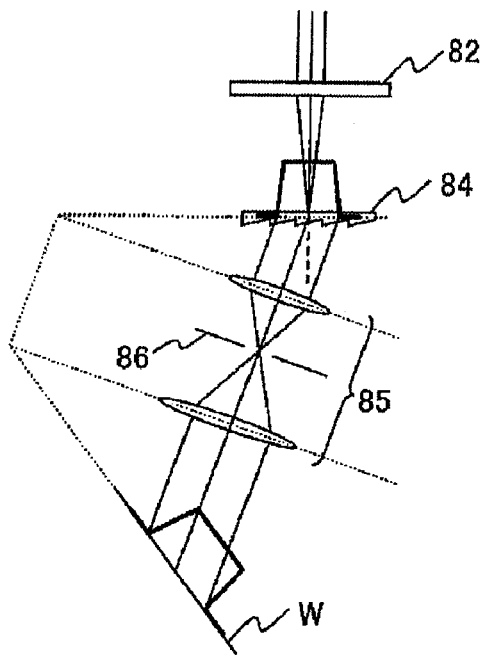
FIG. 35 is a diagram showing a modified example of optical elements comprised in the illumination intensity distribution control part of the defect inspection device according to the present invention.

As another embodiment to avoid deformation of an intermediate image in a construction similar to FIG. 33, a construction using a telecentric imaging system 85 as the imaging system 83 is shown in FIG. 35. An intermediate image of an illumination intensity distribution formed by the illumination intensity distribution forming element 82 is imaged on the sample surface by the telecentric imaging system 85. The telecentric imaging system 85 is configured using a plurality of lenses and an aperture stop 86. By making the telecentric imaging system 85 be a configuration of double telecentric, a variation in magnification due to the imaged height is eliminated and deformation of the illumination intensity distribution on the sample plane can be suppressed. When the double telecentric configuration is adopted, the optical axis of the telecentric imaging system 85 is tilted with respect to the principal optical axis of a light beam incident onto the intermediate image plane as shown in FIG. 35. Therefore, by making a condensing NA of the telecentric imaging system 85 large enough to include the principal optical axis of the light beam incident onto the intermediate image plane, or by providing a diffraction grating 84 on the intermediate image plane as shown in FIG. 35 to bend the light beam after passing through the intermediate image plane to align to the optical axis of the telecentric imaging system 85, light incident on the intermediate image plane is efficiently guided to the sample plane. As the diffraction grating 84, a blazed diffraction grating of the reflection type or the transmission type is suitable and one with a diffraction efficiency of 50% or more in a desired direction is used.

Figure 36:
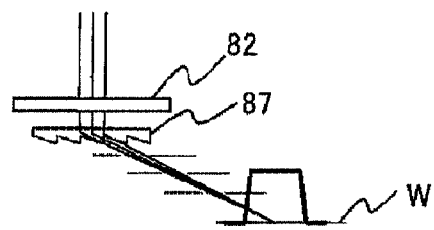
FIG. 36 is a diagram showing a modified example of optical elements comprised in the illumination intensity distribution control part of the defect inspection device according to the present invention.

As another modified example of the illumination intensity distribution control part 7, a construction using an illuminance distribution control element 82 and a diffraction grating 87 is shown in FIG. 36. The illuminance distribution control element 82 has a function of forming a desired illumination intensity distribution in a plane perpendicular to an optical axis. In this case, by installing the diffraction grating 87 downstream of (or immediately before) the illuminance distribution control element 82, the optical axis is bent with respect to the wavefront and a desired illumination intensity distribution is formed on the sample plane tilted with respect to the optical axis. As the illuminance distribution control element 82, a diffraction optical element or an aspherical lens is used. As the diffraction grating 87, a blazed diffraction grating of the reflection type or the transmission type is suitable and one with a diffraction efficiency 50% or more in a desired direction is used.

Figure 37:
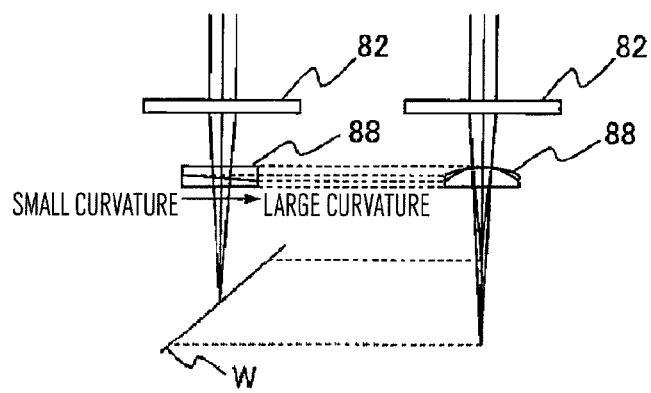
FIG. 37 is a diagram showing a modified example of optical elements comprised in the illumination intensity distribution control part of the defect inspection device according to the present invention.

As another modified example of the illumination intensity distribution control part 7, a construction using the illuminance distribution control element 82 and a conical lens 88 is shown in FIG. 37. The conical lens 88 is a lens of a conical shape or a shape cut out of a part of a conical surface and has a property that a curvature varies with a position in the direction of a ridgeline of the cone. By aligning the direction in which the curvature of the conical lens 88 changes and the incident plane of the optical axis with respect to the sample plane with each other, an image of an illumination intensity distribution can be focused on the sample plane inclined with respect to the optical axis.

Figure 4:
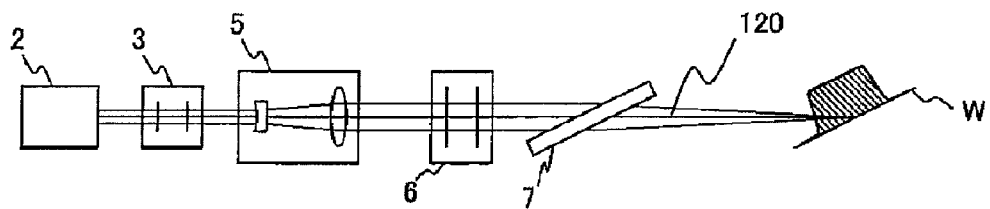
FIG. 4 is a diagram showing a modified example of the shape of the illumination intensity distribution implemented with the illumination unit of the defect inspection device according to the present invention.

As another modified example of the illumination intensity distribution control part 7, an example in which optical elements constructing the illumination intensity distribution control part 7 are installed parallel to the sample plane is shown in FIG. 4. Though for the optical elements arranged in this way performance of condensing off-axis light heavily inclined with respect to the normals of the surfaces of the optical elements is required, condensing becomes easy for the aspect that distances between the surfaces of the optical elements and the sample plane become constant. In the construction of FIG. 4, by using an aspherical lens, an aspherical mirror, a diffractive optical element, or the like which is designed to correct off-axis aberration, it is possible to secure condensing performance of an illumination spot width of 5 µm or less even when an illumination incidence angle to the sample plane is large (larger than the incidence angle of 65 degrees).

Figure 38:
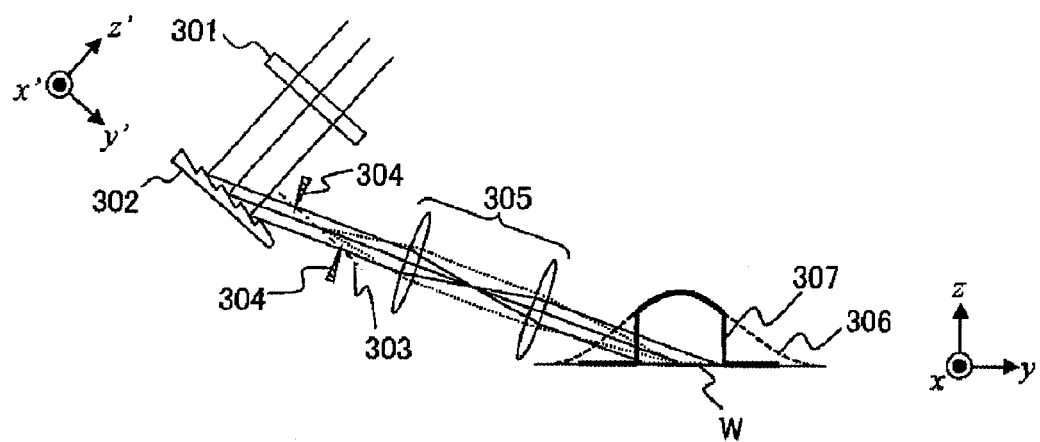
FIG. 38 is a diagram showing an example of the illumination intensity distribution control part of the defect inspection device according to the present invention.

As another modified example of the illumination intensity distribution control part 7, a construction to form a Gaussian distribution illumination with its side lobes cut off is shown in FIG. 38. Collimated light expanded to an arbitrary beam diameter by the beam expander 5 is concentrated into a linear form by a cylindrical lens 301. By disposing a diffraction grating 302 in front of a condensing position, the focal plane due to the cylindrical lens 301 is tilted with respect to the optical axis. Now, the focal plane by the cylindrical lens 301 is supposed to be an intermediate image plane 303. The illumination light an optical axis of which is linearly focused is shielded in its linear longitudinal direction by a shading slit 304 on the intermediate image plane 303 and imaged on the sample plane by an imaging optics system 305. With this construction, an illumination intensity distribution of a profile of a line-shaped Gaussian distribution elongated in one direction with its side lobes cut off is formed.

The cylindrical lens 301 has a curvature in the x' direction of FIG. 38 and the longitudinal and width directions of the line-shaped concentrated light by the cylindrical lens 301 correspond to the y' and x' directions, respectively. In order to converge an illumination spot width down to a form of a thin line of 5 µm or less, it is desirable to construct the cylindrical lens 301 with a plurality of cylindrical lenses or spherical lenses. When a diameter of the beam emitted from the light source 2 is 1 mm, by making the beam expander 5 constructed to magnify by a factor of 20 in the x' direction of FIG. 38 using a cylindrical lens and using one having a curvature in the x' direction and its focal length of 50 mm as the cylindrical lens 301, a line-shaped concentrated light of 1 mm in the longitudinal direction and 1.6 µm in the width direction on the focal plane of the cylindrical lens 301 is obtained (a condensing NA of 0.2 in the x' direction).

The diffraction grating 302 is designed in terms of a pitch of the diffraction grating pitch such that illumination light after passing through the cylindrical lens 301 makes a predetermined incidence angle with respect to the sample plane and installed. By the diffraction grating 302, the focal plane is tilted with respect to the optical axis. In order to increase a diffraction efficiency of a specific order, it is preferable to employ one of the blazed type as the diffraction grating 302. In order to maximize the diffraction efficiency, it is suitable to use first-order diffracted light. The transmission type may be used as the diffraction grating 302. The blazed-type surface roughness of the diffraction grating 302 is formed in the y' direction in FIG. 38 and the diffraction grating 302 can be regarded as flat in the x' direction. Since concentration by the cylindrical lens 301 is in the x' direction, performance of concentration in the width direction of line-shaped concentrated light formed by the cylindrical lens 301 would not be deteriorated by insertion of the diffraction grating 302. With respect to the y' direction in which diffraction occurs by the diffraction grating 302, since collimated light is incident and the width of the incidence angle can be regarded as nearly zero, the diffraction grating 302 may be designed to maximize the diffraction efficiency of the first-order diffracted light for incident light of a specific incidence angle. Hence, higher diffraction efficiency can be obtained than one with optimum design for incident light with a width in the angle.

In FIG. 38 an arrangement where the diffraction grating 302 is installed in front of the intermediate image plane 303 (in a side closer to the light source 2) is shown. The diffraction grating 302 may be installed after the intermediate image plane 303. In these arrangements, as line-shaped concentrated light is defocused to spread out on the diffraction grating 302 and an illumination light power density on the diffraction grating 302 is reduced, damage on the diffraction grating 302 by the illumination light is mitigated. Letting NA of concentrated light by the cylindrical lens 301 be α and a distance between the intermediate image plane 303 and the surface of the diffraction grating be d, the size of spread of a beam on the diffraction grating by defocusing becomes approximately 2αd. As an example, in order to make the beam width on the diffraction grating be 1 mm or more with α=0.2, the distance d needs to satisfy d>2.5 mm. Although it is possible to install the surface of the diffraction grating 302 coincident with the intermediate image plane 303, since in this case an illumination light power density becomes higher than when it is installed off from the intermediate image plane (nearly the same as on the irradiation plane), the diffraction grating 302 tends to be more susceptible to damage and it becomes difficult to let illumination light of a high power enter onto the sample plane. In order to suppress damage onto the diffraction grating 302, it is effective to install an optical system upstream which reduces energy of a single pulse shown in FIGS. 16, 17, and 18. In order to suppress damage onto the diffraction grating 302 such a means is also effective as to blow an inert gas such as nitrogen, argon, or helium on the diffraction grating 302, to cool by means of attaching a Peltier element tightly on the diffraction grating 302, or to purge the vicinity of the diffraction grating 302 with an inert gas such as nitrogen, argon, or helium. In addition, adopting a construction in which an illumination spot of a size larger than an illumination spot created on the sample plane is created on the diffraction grating 302 and the image on the diffraction grating 302 is reduced and projected onto the illumination plane by an imaging optics system 305 is also effective to mitigate damage onto the diffraction grating 302.

The shading slit 304 is installed on the intermediate image plane 303 so as to block part of a line-shaped Gaussian beam concentrated by the cylindrical lens 301 in its longitudinal direction. When the diameter (the 1/e^2 diameter) of the Gaussian beam in the longitudinal direction is denoted by D, a power density r (a relative value while letting a power density at the center of the beam be 1) at a distance L from the center of the beam is expressed by MATH. 4 as follows.

$$r = \exp\left[-8\left(\frac{L}{D}\right)^2\right] \quad \text{[MATH. 4]}$$

When it is desired to cut off side lobes of the Gaussian beam at positions where a relative value of the power density with respect to the center of the beam is r (0<r<1), the shading slit 304 should be installed to shield the light at a position away from the center of the beam by the distance L obtained by MATH. 5.

$$L = D\sqrt{-\frac{\log r}{8}} \quad \text{[MATH. 5]}$$

When a diameter (a 1/e^2 diameter) D of the Gaussian beam in the longitudinal direction is equal to 1 mm, for example, by placing the shading slit 304 at the distance L from the center of the beam equal to 0.253 mm, a Gaussian beam with its side lobes cut off at positions of a relative intensity of 0.6 with respect to the center of the beam is obtained. A power density at a position outside where the side lobes are cut off becomes very small with respect to the center of the beam (1/1,000 or less with respect to the center of the beam).

Figure 40:
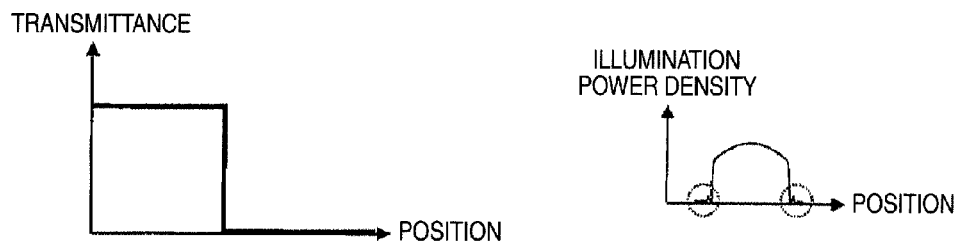
FIG. 40 contains a graph showing a relationship between a position and a transmittance and a graph showing a relationship between a position and an illumination density power.
Figure 41:
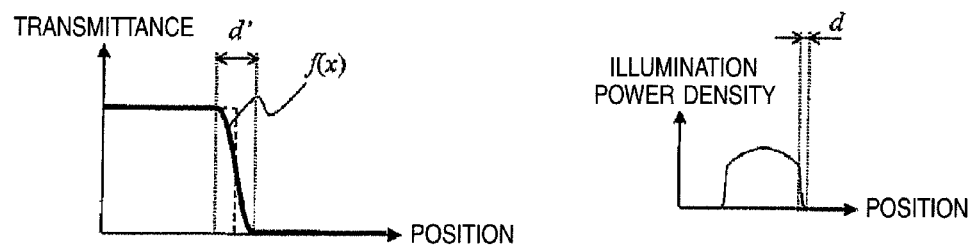
FIG. 41 contains a graph showing a relationship between a position and a transmittance and a graph showing a relationship between a position and an illumination density power.

As shown in FIG. 40, when one having two values of transmittance of completely transmitting and completely shielding is used as the shading slit 304, ringing tends to take place at ends of an illumination power density distribution generated on the irradiation plane as an influence of occurrence of diffraction between the transmitting part and the shielding part. As shown in FIG. 41, when one for which a transmittance varies continuously from the transmitting part to the shielding part is used as the shading slit 304, diffraction is suppressed between the transmitting part and the shielding part and thus ringing in the vicinity of ends of the illumination power density distribution generated on the irradiation plane is suppressed. From this, in inspection in the vicinity of the ends of an inspection target of a semiconductor substrate or the like, influences of scattered light noise from the substrate edge can be mitigated.

When a transmittance in a zone where the transmittance varies continuously is assumed to be a function of a position, f(x), it is desired the shape of the function f(x) is a smooth shape having as little high frequency components as possible in order to suppress diffracted light, and a Gaussian function, a Hanning window function, a Blackman window function, or a shape similar to these functions is used. By letting the width of the zone where the transmittance varies continuously be d', when d' is small (from about the illumination wavelength to about several times of the illumination wavelength), the variation of the transmittance is sharp and diffracted light tends to be generated. When the optical magnification of the imaging optics system 305 is unity, a spread d of an end of the illumination light intensity distribution on the sample surface also becomes nearly the same as d', whereby inspection with a high sensitivity becomes possible up to a region of the distance d' from the edge of the inspection target. Thus, by letting the illumination wavelength be λ, when it is desired to restrain an area at the edge of the inspection target which is unable to be inspected at a distance of 0.5 mm or less from the edge, it is preferable that a range of the width d' of the zone where the transmittance varies continuously would be 10λ or more and 0.5 mm or less (if λ is 0.4 μm, 4 μm<d<500 μm).

The illumination light intensity distribution on the intermediate image plane 303 is focused into an image on the sample surface by the imaging optics system 305. The imaging optics system 305 has a condensing NA equivalent to or greater than a collection angle of the illumination light by the cylindrical lens 301 or a collection angle of the illumination light after passing through the diffraction grating 302. A relationship among the intermediate image plane 303, the principal plane of the lens of the imaging optics system 305, and the sample surface follows a relationship of Scheimpflug. In order to suppress aberrations, the imaging optics system 305 is constructed with a plurality of spherical lenses or aspherical lenses. By making the imaging optics system 305 be a configuration of double telecentric, the optical magnification of the imaging optics system 305 becomes substantially constant regardless of the position in the y direction in FIG. 38 and the width of the beam on the sample plane becomes constant regardless of the position in the y direction. Or even when the imaging optics system 305 is not made to be double telecentric, by making the focal length of the imaging optics system 305 long compared with the imaged height of the illumination light in the intermediate image plane, the angle of view becomes small and thus a variation in the magnification which depends upon a position in the y direction can be reduced. When the imaged height (a position in the y direction) of the illumination light in the intermediate image plane 303 is 0.5 mm, by setting the focal lengths of the objective lens and the imaging lens in the imaging optics system 305 to be equal to or longer than 50 mm, a variation in the optical magnification (the lateral magnification) due to the imaged height is suppressed to be within 1%.

Figure 39:
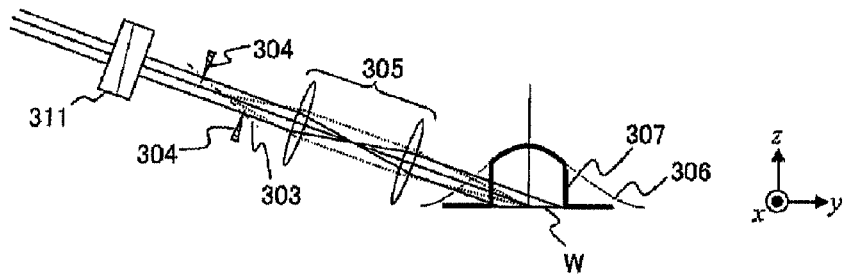
FIG. 39 is a diagram showing a modified example of the illumination intensity distribution control part of the defect inspection device according to the present invention.

As another modified example of the illumination intensity distribution control part 7, a construction to form a Gaussian distribution illumination with its side lobes cut off using a conical lens is shown in FIG. 39. It is a construction in which the functions of the cylindrical lens 301 and the diffraction grating 302 shown in FIG. 38 are replaced with a conical lens 311. Since a diffraction grating is not used, it has advantages that loss of an illumination power is small, that an issue of damages onto the diffraction grating can be avoided, and the like. The conical lens 311 is a lens of a conical shape or a shape cut out of a part of a conical surface and has a property that a curvature varies, that is, a focal length varies with a position in the direction of a ridgeline of the cone. By making the direction in which the focal length of the conical lens 311 changes parallel to the y direction of FIG. 39, a line-shaped Gaussian distribution can be focused on the intermediate image plane 303 inclined with respect to the optical axis. Instead of the conical lens 311, an aspherical lens (a free-form-surface lens) with a focal length varying with a light-beam passing location in the y direction may be employed.

Assuming that the optical magnification of the imaging optics system 305 is unity, the length of the illumination spot in the y direction is l, the average focal length of the conical lens 311 is L, and the illumination incidence angle to the sample surface is θ, then a rate of change δ of the focal length of the conical lens 311 is obtained approximately as δ=l×sin θ/L. Here, δ is a ratio of a difference between the maximum focal length and the minimum focal length to the average focal length in the conical lens 311. Since δ is equal to the rate of change of the width of the line-shaped Gaussian beam in the y direction on the sample plane, it is desirable that δ is small in order to inspect the sample plane with a uniform sensitivity. When l=1 mm and θ=75 degrees, δ is suppressed to 2% or less by securing L of 48 mm or longer.

According to the constructions shown in FIGS. 35, 36, 37, 38, and 39, large off-axis aberrations will not be generated even when the illumination incidence angle to the sample surface is large (larger than an incidence angle of 65 degrees) since the optical elements for concentrating and imaging the illumination light remain perpendicular to the optical axis regardless of the illumination incidence angle with respect to the sample plane. For this reason, the optical elements for concentrating and imaging the illumination light in these constructions can be inexpensively constructed with spherical lenses, spherical mirrors, and their combinations.

Figure 42:
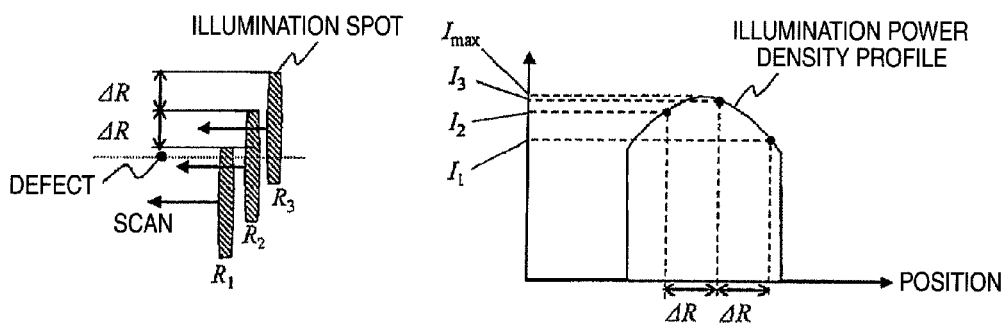
FIG. 42 contains diagrams schematically showing a scan locus of an illumination spot with respect to a defect.

Explanation is given with reference to FIG. 42 on a method for obtaining a stable detection sensitivity regardless of a relative position of a defect with respect to an illumination spot when part of Gaussian distribution illumination is used as illumination for inspection as shown in FIGS. 38 and 39. Scan loci of the illumination spot with respect to a defect are schematically shown in a left side of FIG. 42. By making an amount of movement ΔR in a radial direction per turn be 1/N of the illumination spot length in the spiral scanning shown in FIG. 20, a single defect passes within the illumination spot N times and a signal for the single defect is detected N times. In FIG. 42 an example of N=3 is shown. Detection signal intensities I1, I2, and I3 for respective rotations R1, R2, and R3 are schematically shown in the right side of FIG. 42. Since the profile of the illumination power density is known from design values or actual measurement values by the illumination intensity distribution monitor 24, by inversely calculating a corresponding illumination power density profile thereto based on the plurality of detection signal intensities I1, I2, and I3, a signal value Imax as to the case where the defect supposedly passes through the center of the illumination power density profile can be estimated. From this, variations in the inspection sensitivity due to variations in the detection signals caused by different defect passing positions with respect to the illumination spot can be reduced. Incidentally, in the case of the Gaussian distribution illumination, since an illumination power density profile corresponding to a detection signal can be represented by two parameters of the maximum value and the beam position (assuming that the beam diameter is known), using two signals detected with N=2 enables estimation in principle; however, since noise is included in actual detection signals, estimating Imax using three detection signals with N=3 improves an estimation accuracy and reduces variations in inspection sensitivity. By making N larger improves the estimation accuracy, but reduces the inspection rate correspondingly.

Figure 5:
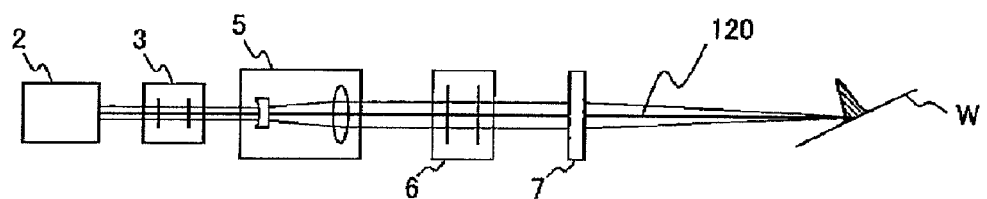
FIG. 5 is a diagram showing a modified example of the shape of the illumination intensity distribution implemented with the illumination unit of the defect inspection device according to the present invention.
Figure 6:
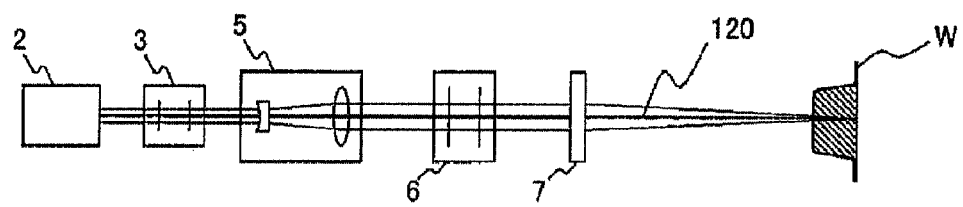
FIG. 6 is a diagram showing a modified example of the shape of the illumination intensity distribution implemented with the illumination unit of the defect inspection device according to the present invention.

As another modified example of the illumination intensity distribution control part 7, a modified example in which a uniform illumination intensity distribution is generated in a plane which includes the normal to the sample surface and is perpendicular to the incidence plane of the oblique incidence illumination is shown in FIGS. 5 and 6. Since the illumination intensity distribution is made uniform in the plane perpendicular to the axis of the illumination light as shown in FIG. 6, there is an advantage that the formation of the uniform illumination intensity distribution is easier than the constructions of FIGS. 2 and 3. However, since the direction of the short diameter of the illumination spot and the direction of the position shift of the illumination spot due to a displacement of the sample surface height match with each other, a coordinate accuracy for the detected defect is reduced. In order to suppress it, holding of the sample by suction of the entire surface of the back face of the sample or low-speed scan is carried out in the stage 103 so as to reduce the displacement of the sample surface height.

Figure 18:
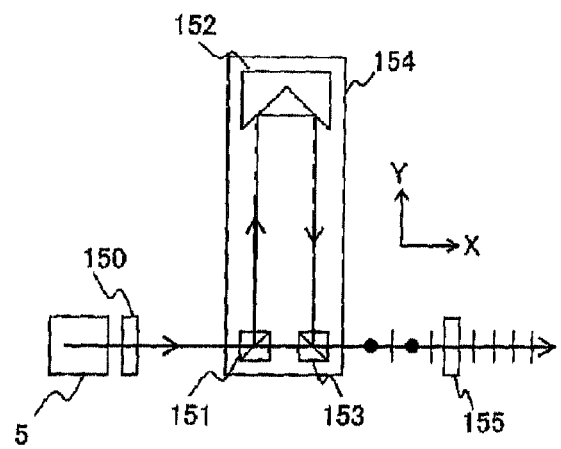
FIG. 18 is a diagram showing a modified example of the means for reducing an energy per single pulse with the optical path branching and the optical path combining in the illumination unit of the defect inspection device according to the present invention.

Explanation is given as to a modified example of branching/combining of optical paths shown in FIG. 16 using FIG. 18. When the optical path branching/combining shown in FIG. 16 is carried out, it becomes an unpolarized state after combining of the two optical paths by superposing polarized components of two directions which do not mutually interfere, and, when linearly polarized light is generated in the polarization control part 6 at a later stage, loss of the illumination energy arises. Thus, as a modified example, by using a polarization modulation element 155 which can switch over temporally between polarized states of transmitted light, polarized states of all pulses can be equalized and linear polarization can be generated without loss of the illumination energy as shown in FIG. 18. As the polarization modulation element 155, a photoelastic modulator (PEM: Photoelastic Modulator), a liquid crystal element, an electro-optical modulator, an acousto-optical modulator, or the like is employed.

REFERENCE SIGNS LIST

2: laser light source, 3: attenuator, 4: exit light adjustment part, 5: beam expander, 6: polarization control part, 7: illumination intensity distribution control part, 7v: illumination intensity distribution control part, 22: beam monitor, 23: beam monitor, 24: illumination intensity distribution monitor, 53: control unit, 54: display unit, 55: input unit, 101: illumination unit, 102: detection unit, 103: stage, 105: signal processing unit, 120: axis of illumination light, 201: objective lens, 202: polarizing filter, 203: imaging lens, 204: multi-pixel sensor, 205: conjugate plane of sample plane

The invention claimed is:

1. A defect inspection device comprising:
an irradiating unit, the irradiating unit comprising:
an illumination light adjusting unit which adjusts light emitted from a light source into illumination light having predetermined irradiation conditions; and
an illumination intensity distribution control unit which controls an illumination intensity so that an illumination intensity in a predetermined detection target area out of an illumination area on a surface of a sample on which the illumination light is irradiated is 50% or more of an illumination intensity at a center position of the illumination light on a surface of the sample and an illumination intensity in an illumination area other than the predetermined detection target area is 0.1% or less of an illumination intensity at a center position of the illumination light on a surface of the sample;
a scanning unit which scans the sample in a direction perpendicular to a longitudinal direction of the illumination area in the irradiating unit;
a detecting unit which detects scattered light generated from a surface of the sample due to illumination light irradiated by the irradiating unit; and
a determining unit, the determining unit comprising:
a defect presence/absence determining unit which processes a detection signal based on scattered light from a surface of the sample detected by the detecting unit and determines presence/absence of a defect on a surface of the sample; and
a defect dimension determining unit which determines, when presence of a defect is determined by the defect presence/absence determining unit, a dimension of the defect;
wherein the illumination intensity distribution control unit comprises:
a light-shielding unit which shields part of an illumination intensity distribution at a position of an intermediate image corresponding to a center position of the illumination light; and
an imaging unit which forms the intermediate image on a surface of the sample.

2. The defect inspection device according to claim 1, wherein, in the detecting unit, a plurality of scattered light beams scattering due to illumination light irradiated by the irradiating unit, from a surface of the sample, and in mutually different directions are detected, and a detection signal based on the plurality of scattered light beams is detected.

3. The defect inspection device according to claim 1, wherein, in the illumination intensity distribution control unit, an illumination intensity distribution provided to a surface of the sample is a distribution in a longitudinal direction of the illumination area, which includes a center of a Gaussian distribution and in which an intensity distribution of skirts of a Gaussian distribution away from a center by a desired distance or more is reduced.

4. The defect inspection device according to claim 1, wherein, in the scanning unit, an amount of scan of the sample is made shorter than a length of an illumination intensity distribution on a surface of the sample obtained by the illumination intensity distribution control unit and scan is performed so that a same defect passes through a plurality of positions mutually different on an illumination intensity distribution.

5. A defect inspection method which comprises:
an irradiating step, the irradiating step comprising:
an illumination-light adjusting step for adjusting light emitted from a light source into illumination light having predetermined irradiation conditions; and
an illumination-intensity-distribution controlling step for controlling an illumination intensity so that an illumination intensity in a predetermined detection target area out of an illumination area on a surface of a sample on which the illumination light is irradiated is 50% or more of an illumination intensity at a center position of the illumination light on a surface of the sample and an illumination intensity in an illumination area other than the predetermined detection target area is 0.1% or less of an illumination intensity at a center position of the illumination light on a surface of the sample;
a scanning step for scanning the sample in a direction perpendicular to a longitudinal direction of the illumination area in the irradiating step;
a detecting step for detecting scattered light generated from a surface of the sample due to illumination light irradiated by the irradiation step; and
a determining step, the determining step comprising:
a defect-presence/absence-determining step for processing a detection signal based on scattered light from a surface of the sample detected in the detecting step and determining presence/absence of a defect on a surface of the sample; and
a defect-dimension-determining step for determining, when presence of a defect is determined in the defect-presence/absence-determining step, a dimension of the defect;
wherein the illumination-intensity-distribution controlling step comprises:
a light-shielding step for shielding part of an illumination intensity distribution at a position of an intermediate image corresponding to a center position of the illumination light; and
an imaging step for forming the intermediate image on a surface of the sample.

6. The defect inspection method according to claim 5, wherein, in the detecting step, a plurality of scattered light beams scattered due to illumination light irradiated in the irradiating step, from a surface of the sample, and in mutually different directions are detected, and a detection signal based on the plurality of scattered light beams is detected.

7. The defect inspection method according to claim 5, wherein, in the illumination-intensity-distribution controlling step, the illumination intensity distribution provided to a surface of the sample is a distribution in a longitudinal direction of the illumination area, which includes a center of a Gaussian distribution and in which an intensity distribution of skirts of a Gaussian distribution away from a center by a desired distance or more is reduced.

8. The defect inspection method according to claim 5, wherein, in the scanning step, an amount of scan of the sample is made shorter than a length of an illumination intensity distribution on a surface of the sample obtained in the illumination-intensity-distribution controlling step and scan is performed so that a same defect passes through a plurality of positions mutually different on an illumination intensity distribution.

* * * * *